United States Patent [19]

Fitzmaurice et al.

[11] Patent Number: 5,705,624
[45] Date of Patent: Jan. 6, 1998

[54] DNA SEQUENCES ENCODING ENZYMES USEFUL IN PHYTOENE BIOSYNTHESIS

[76] Inventors: Wayne Paul Fitzmaurice, 1218 Las Encinas Ct., Vacaville, Calif. 95687; Gary Mark Hellmann, 3516 Donegal Dr., Clemmons, N.C. 27012; Laurence Kay Grill, 3570 Cantelow Rd., Vacaville, Calif. 95688; Monto Hiroshi Kumagai, 1330 Brown Dr., Davis, Calif. 95616; Guy Richard della-Cioppa, 814 Derry Cir., Vacaville, Calif. 95688

[21] Appl. No.: 579,667

[22] Filed: Dec. 27, 1995

[51] Int. Cl.$^6$ ............................ C07H 21/04; C12N 9/00
[52] U.S. Cl. ........................ 536/23.2; 435/183; 536/23.6
[58] Field of Search ........................... 536/23.2, 23.6; 435/183

[56] References Cited

U.S. PATENT DOCUMENTS

| | | | |
|---|---|---|---|
| 5,304,478 | 4/1994 | Bird et al. | 435/172.3 |
| 5,328,845 | 7/1994 | Finkelstein et al. | 435/254.1 |
| 5,365,017 | 11/1994 | Chappell et al. | 800/205 |
| 5,429,939 | 7/1995 | Misawa et al. | 435/67 |
| 5,545,816 | 8/1996 | Ausich et al. | 800/205 |
| 5,589,581 | 12/1996 | Misawa et al. | 536/23.2 |
| 5,618,988 | 4/1997 | Hauptmann et al. | 800/205 |

FOREIGN PATENT DOCUMENTS

| | | |
|---|---|---|
| WO 91/13078 | 9/1991 | WIPO. |
| WO 92/06206 | 4/1992 | WIPO. |

OTHER PUBLICATIONS

Hugueney, P. et al., "Characterization and molecular cloning of flavoprotein catalyzing the synthesis of phytofluene and ζ-carotene in Capsium chromoplasts", Eur. J. Biochem., vol. 209, pp. 399–407 (1992).

Scolnik, P. A. et al., "Phytoene Desaturase from Arabidopsis", Plant Physiol., vol. 103, No. 4, p. 1 (1993).

Linden, H. et al., "Immunogold localization of phytoene desaturase in higher plant chloroplasts", Physio Plantarum, vol. 88, pp. 229–236 (1993).

Pecker, I. et al., "A single polypeptide catalyzing the conversion of phytoene to ζ-carotene is transcriptionally regulated during tomato fruit ripening", Proc. Natl. Acad. Sci. USA, vol. 89, pp. 4962–4966 (1992).

J. Ray et al.; Sequence of pTOM5, a ripening related cDNA from tomato, Nucleic Acids Research, 15, No. 24:10587 (1987).

G. Sandmann; Carotenoid biosynthesis in microorganisms and plants, Eur. J. Biochem. 223:7–24 (1994).

S. Römer et al.; Expression of the Genes Encoding the Early Carotenoid Biosynthesis Enzymes in Capsicum Annuum, Biochem. Biophys. Res. Comm. 196:1414–1421 (1993).

P. A. Scolnik et al.; Nucleotide Sequence of an Arabidopsis cDNA for Phytoene Synthase, Plant Physiol. 104:1471–1472 (1994).

Bartley et al. (1992) A tomato gene expressed during fruit ripening encodes an enzyme of the carotenoid biosynthesis pathway. J. Biol. Chem. 267: 5036–5039, Mar. 1992.

Rudinger, J. (1976) Characteristics of the amino acids as components of a peptide hormone sequence. In: Peptide Hormones, Ed. J. A. Parsons, pp. 1–7, Jun. 1976.

*Primary Examiner*—Robert A. Wax
*Assistant Examiner*—Einar Stole

[57] ABSTRACT

DNA sequences isolated from Nicotiana species (e.g., *Nicotiana tabacum* and *Nicotiana benthamiana*) and encoding polypeptides having enzymatic activity for producing phytoene, and the polypeptides encoded, are provided.

4 Claims, 2 Drawing Sheets

5,705,624

1

DNA SEQUENCES ENCODING ENZYMES USEFUL IN PHYTOENE BIOSYNTHESIS

FIELD OF THE INVENTION

The present invention relates to genetic engineering, and in particular to DNA sequences encoding enzymes for catalyzing the biosynthesis of carotenoids, such as phytoene.

BACKGROUND OF THE INVENTION

Carotenoids are 40-carbon terpenoids having eight connected isoprene units. Carotenoids include phytoene, zeta-carotene, lycopene, beta-carotene, zeaxanthin and zeaxanthin diglucoside. See Krinsky et al., *Carotenoids: Chemistry and Biology*, Plenum Press, pp. 279–291 (1990) and Nes et al., *Regulation of Isopentenoid Metabolism*, ACS Sym. Ser. 497 (1992). A biosynthetic pathway for the various carotenoids is set forth in U.S. Pat. No. 5,304,478, European Patent Application No. 393,690 and PCT WO 91/13078, which are incorporated herein in their entirety by reference.

Certain carotenoids can be considered intermediates in the biosynthetic pathway of other carotenoids. Carotenoids such as phytoene have been found to have a useful application in absorbing ultraviolet radiation. See U.S. Pat. No. 4,642,318. Furthermore, the carotenoid lycopene has been found to have use as a coloring agent in situations in which a red color is desired. See Taylor, *Carotenoids: Products, Applications and Markets*, Decision Resources, Inc. (1990). Other biosynthetically produced carotenoids have found use as coloring agents, particularly for foods, in situations in which an orange or yellow color is desired. Carotenoids also have been found to be useful as animal feeds, as well as in the pharmaceutical and cosmetics industries. See Taylor, *Carotenoids: Products, Applications and Markets*, Decision Resources, Inc. (1990), and E-Siong Tee, *Crit. Rev. Food Sci and Nutri.*, Vol. 31, p. 103 (1992).

Phytoene synthase genes have been cloned from Lycopersicon (Ray et al., *Nucleic Acids Res*, Vol. 15, p. 10587 (1987)), and also recently from Capsicum (Römer et al., *Biochem Biophys Res Commun*, Vol. 196, pp. 1414–1421 (1993)), and from *Arabidopsis* (Scolnik and Bartley, *Plant Physiol*, Vol. 104, pp. 1471–1472 (1994)). A review of the cloning of carotenoid biosynthetic genes is contained in Sandmann, Eur J Biochem, Vol. 223, pp. 7–24 (1994). However, no phytoene synthase sequences have been reported from any Nicotiana species.

It would be highly desirable to have the capability to alter the biosynthetic pathway for carotenoids, particularly in higher plants such as the solanaceae. As such, it would be desirable to provide nucleotide sequences that encode enzymes useful in the carotenoid biosynthesis pathway, such as phytoene synthase. In particular, it would be desirable to provide the nucleotide sequences that encode phytoene synthase from a higher plant species, such as a Nicotiana species. It also would be desirable to provide unique nucleotide sequences to provide broader opportunities for controlling the spectrum of expression in various transgenic organisms.

SUMMARY OF THE INVENTION

A first aspect of the present invention is a nucleotide sequence isolated from a Nicotiana species and encoding a polypeptide which has enzymatic activity for producing phytoene.

A further aspect of the present invention is a nucleotide sequence encoding a polypeptide having enzymatic activity for producing phytoene, the sequence selected from among (a) SEQ ID NO: 1, SEQ ID NO:3, SEQ ID NO:5, SEQ ID NO:7 and SEQ ID NO:9; (b) nucleotide sequences which encode a polypeptide having enzymatic activity for producing phytoene and which hybridize to the sequences of (a) above under stringent conditions defined by a wash stringency of 0.3M NaCl, 0.03M sodium citrate, 0.1% SDS at 70° C.; and (c) nucleotide sequences which encode a polypeptide having enzymatic activity for producing phytoene and which differ from sequences of (a) and (b) due to the degeneracy of the genetic code.

A further aspect of the present invention is a nucleotide sequence encoding a polypeptide which has enzymatic activity for producing phytoene, the polypeptide having an amino acid sequence of SEQ ID NO:2, SEQ ID NO:4, SEQ ID NO:6 or SEQ ID NO:8.

A further aspect of the present invention is a polypeptide having enzymatic activity for producing phytoene and having an amino acid sequence selected from SEQ ID NO:2, SEQ ID NO:4, SEQ ID NO:6 and SEQ ID NO:8.

The foregoing and other objects and aspects of the present invention are explained in detail in the specification set forth below.

DETAILED DESCRIPTION OF THE INVENTION

Figure 1:
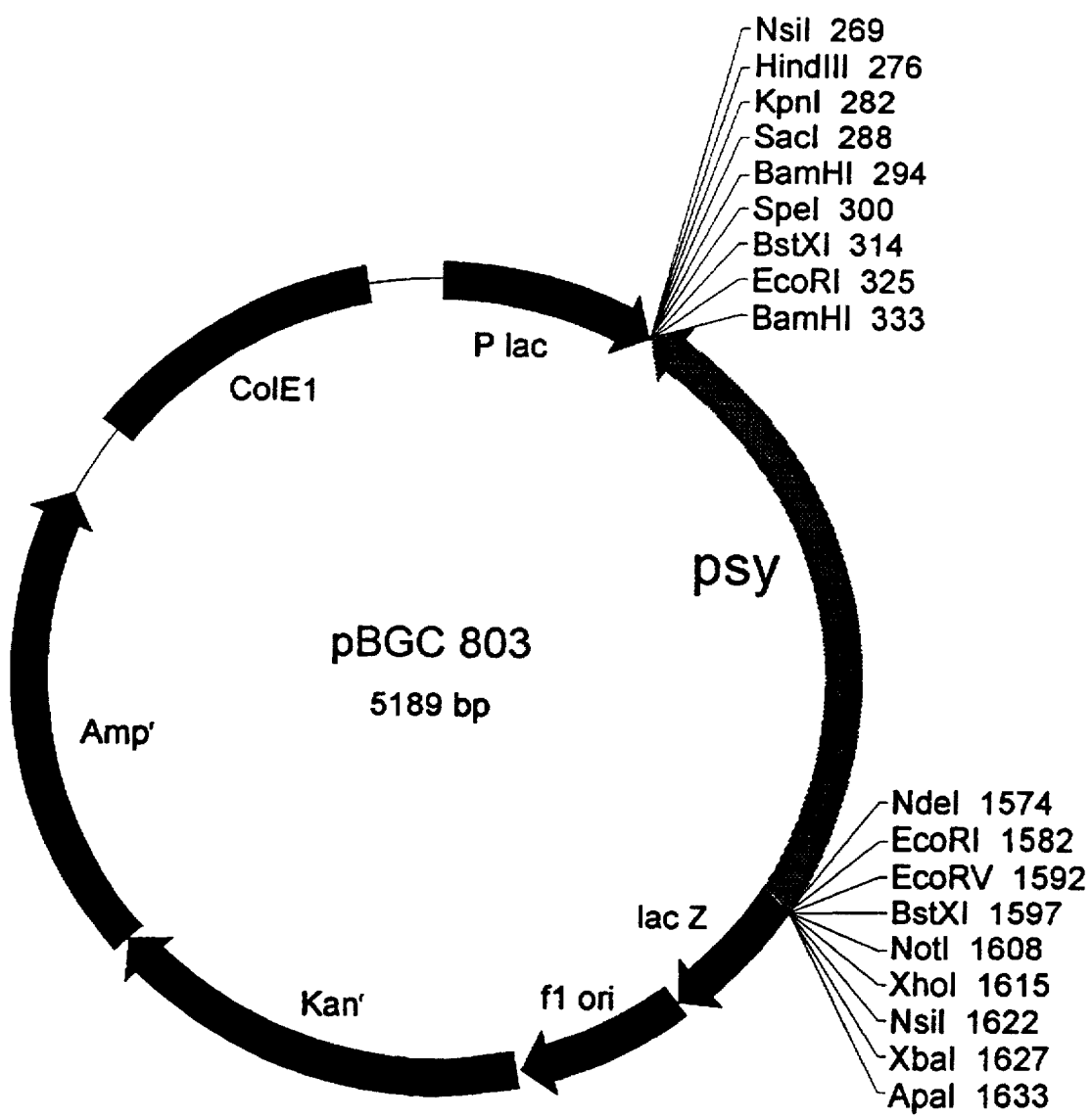
FIG. 1 is a map of the plasmid pBGC803, which contains the *N. benthamiana* phytoene synthase coding sequence from SEQ ID NO:3 cloned into pCRII (Invitrogen, San Diego, Calif.).

The present invention relates to nucleotide sequences (DNA or RNA molecules) capable of encoding a polypeptide which has enzymatic activity for producing a carotenoid (e.g., phytoene). Such a polypeptide which has enzymatic activity for producing phytoene is referred to as phytoene synthase. The DNA is isolated from a Nicotiana species, such as *Nicotiana benthamiana* or *Nicotiana tabacum*. The nucleotide sequences specified herein as SEQ ID NOS: 1, 3, 5 and 7 encode all of the enzyme phytoene synthase, and variants of those sequences encode enzymes exhibiting the same biological activity as phytoene synthase. Such nucleotide sequences correspond to, or substantially to, the DNA sequences specified in SEQ ID NOS: 1, 3, 5 and 7. The nucleotide sequence specified in SEQ ID NO:9 is a partial phytoene synthase sequence. The nucleotide sequences may be provided as DNA or RNA molecules in an isolated, substantially pure form. The DNA sequences specified in SEQ ID NOS: 1 and 3 were isolated from *Nicotiana benthamiana*. The DNA sequences specified in SEQ ID NOS: 5, 7 and 9 were isolated from *Nicotiana tabacum*. The present invention also relates to nucleotide sequences (DNA or RNA molecules) that selectively hybridize to those nucleotide sequences which correspond to the DNA sequences specified in SEQ ID NOS: 1, 3, 5, 7 and 9.

The present invention also relates to certain polypeptides which may be provided in a purified (e.g., isolated and substantially pure) form. The polypeptides have enzymatic activity for producing phytoene and are encoded by nucleotide sequences which correspond to, or substantially to, those sequences specified in SEQ ID NOS: 1, 3, 5 and 7.

Those polypeptides have amino acid sequences which correspond to, or substantially to, those amino acid sequences specified in SEQ ID NOS: 2, 4, 6 and 8, respectively. Polypeptides having amino acid sequences which correspond substantially to those encoded by the specified sequences have different amino acid sequences (e.g., a minor number of amino acids of the sequence can be deleted, added or substituted), but the same type of biological activities as those encoded by the specified sequences, although those biological activities may differ in degree.

The present invention also relates to fragments of polypeptides (e.g., polypeptide derivatives) encoded by nucleotide sequences which correspond to, or substantially to, certain nucleotide subsequences contained within those sequences specified in SEQ ID NOS: 1, 3, 5 and 7. Such fragments represent domains of the full length (i.e., intact) polypeptides. Such fragments can be, for example, transit peptides useful for directing polypeptides to subcellular compartments, or polypeptide domains having such properties as catalytic activity, substrate binding activity, and the like.

Any of the nucleotide sequences of the present invention can be incorporated (i.e., in an operative fashion) into heterologous systems (e.g., yeast, bacteria or certain plants) in order that the respective polypeptides can be synthesized thereby. The nucleotide sequences can be incorporated into plants (e.g., rice, corn, tobacco or tomato), using transformation techniques or viral gene expression systems. The RNA molecules or polypeptides encoded by those nucleotide sequences can be used to alter the biosynthetic pathway of carotenoids and related compounds, or the polypeptides can be isolated in order to be used as enzymes in the in vitro synthesis of carotenoids.

The present invention also relates to recombinant DNA or RNA molecules. Such molecules include DNA sequences, corresponding RNA sequences, or subsequences of such DNA and RNA sequences. Such sequences and subsequences (e.g., promoters, enhancers, terminators and replication signals) are capable of facilitating the expression of RNA molecules or enzymes useful for altering carotenoid biosynthesis. These DNA sequences or subsequences have nucleotide sequences which include, or substantially include, at least one of those sequences specified in SEQ ID NOS: 1, 3, 5, 7 and 9. These DNA sequences may be obtained or isolated from a Nicotiana species, or may originate from unrelated organisms.

The recombinant molecule can be considered a plasmid or a vector. The recombinant molecule can be a plasmid or vector tailored for transfer of the recombinant molecule to plant or other cells. Recombinant molecules also can be contained in a transgenic plant cell, such as a tobacco plant cell.

The invention also relates to the delivery and expression of sequences or subsequences as described in SEQ ID NOS: 1, 3, 5, 7 and 9 via transient virus-based gene delivery systems. Such a system is described in U.S. Pat. No. 5,316,931 and European Patent Application No. 406,267, which are incorporated herein in their entirety by reference. Such a system involves delivery of a selected nucleotide sequence as part of, or in conjunction with, a self-replicating DNA or RNA molecule (e.g., a virus), such that the exogenous gene is replicated and expressed during the course of replication and expression of viral or virus-based nucleic acids and proteins. Such gene delivery systems may be used for expression of nucleic acid sequences or subsequences as described in SEQ ID NOS: 1, 3, 5, 7 and 9 in either sense orientation for the expression of polypeptides, or in antisense orientation for the delivery of RNA molecules capable of inhibiting expression of the target gene or other homologous genes. Genes or gene sequences delivered in such a manner are considered to be functionally inserted in the target organism such as a tobacco plant.

Another aspect of the present invention is a crop composed of a plurality of plants having the nucleotide sequences of the present invention functionally inserted therein, and planted together in an agricultural field, including a greenhouse.

Compositions including genetic sequences and subsequences encoding carotenoid enzymes for expression in plants, such as tobacco plants, impart those plants with the ability to produce altered levels of carotenoids. As such, a method for altering the synthesis of carotenoids in plants involves inserting a recombinant genetic construct into plant cells. Such a construct can provide for synthesis of naturally occurring carotenoids within such plant cells. For example, certain recombinant genetic constructs of the present invention are capable of expressing at least one naturally occurring enzyme in order that resulting transformed plants exhibit enhanced ability to produce carotenoids. As such, there is provided a method for altering the synthetic pathway of carotenoids in plants.

The present invention also relates to antisense sequences for those sequences which correspond to, or substantially to, the totality or a subset of those nucleic acid sequences specified in SEQ ID NOS: 1, 3, 5, 7 and 9. As such, those sequences encode RNA molecules capable of inhibiting expression of the corresponding and related genes. As such, the present invention provides for a method for altering the synthetic pathway of carotenoids. For example, the expression of an antisense molecule may be useful for preventing synthesis of a given carotenoid. Alternatively, expression of an antisense molecule may be useful in accumulating relatively high levels of certain molecules upstream of a particular metabolic block. Another example is the use of such antisense molecules to deliberately direct metabolites toward one branch of a branched pathway. It is important in applying antisense technology to use the antisense of the sequence of interest. While it is sometimes possible to succeed in using antisense fragments from a gene isolated from a highly homologous organism, success is much more likely if the entire identical nucleotide sequence is available for use in attempting antisense. Not all fragments of a gene exhibit function as antisense. However, in some cases, the segment of a gene most effective for antisense is a segment that has limited homology with genes isolated from other organisms.

1. Nucleotide Sequences

The nucleotide sequences of genetic materials of the present invention are endogenous to a Nicotiana species and are isolated from Nicotiana species. Most preferably, the nucleotide sequences are isolated from *Nicotiana benthamiana* or *Nicotiana tabacum*. Examples of other Nicotiana species include *Nicotiana debneyi*, *Nicotiana glauca*, *Nicotiana glutinosa*, *Nicotiana rustica*, and *Nicotiana svaveolens*. Examples of cultivars of *Nicotiana tabacum* include flue-cured tobacco (e.g., NK 326), Burley tobacco (e.g., KY 14) and Maryland tobacco (e.g., MD 609).

As used herein, "native" or "natural" nucleotide sequences refer to those which are endogenous to the organism from which they are isolated, in comparison to sequences which can be produced only by genetic engineering techniques. Native Nicotiana sequences thus are sequences found in plants of the genus Nicotiana. It will be apparent to those skilled in the art that once an endogenous sequence is identified, molecules embodying that sequence can be either isolated from the organism or produced by genetic engineering techniques.

The nucleotide sequence of isolated genetic material of the present invention can be obtained by a variety of techniques. The sequence can be obtained by sequencing non-vector nucleotide sequences of recombinant molecules. Nucleotide sequence information can be obtained by employing widely used DNA sequencing protocols, such as Maxam and Gilbert sequencing, dideoxy nucleotide sequencing, and the like. Examples of suitable nucleotide sequencing protocols can be found in Berger and Kimmel, *Methods in Enzymology Vol.* 51, *Guide to Molecular Cloning Techniques*, Academic Press (1987). Nucleotide sequence information from several recombinant DNA isolates, including isolates from both cDNA and genomic libraries, can be combined so as to provide the entire amino acid coding sequence, as well as the nucleotide sequences of upstream and downstream nucleotide sequences.

For gene isolation, mRNA is converted into cDNA, and the resulting cDNA is cloned. The cloned cDNA then can be used directly, or it, or sequences derived from it, can be utilized for acquiring the entire gene, either (i) from a library (e.g., in a lambda or plasmid vector) using sequence information to screen the library and detect the desired clone, or (ii) by amplification with PCR (i.e., polymerase chain reaction) and subsequent cloning into a suitable vector. For example, the 5' and 3' RACE (Rapid Amplification of cDNA Ends) reactions can be used to clone overlapping 5' and 3' ends of the gene of interest with subsequent assembly of the complete gene.

Nucleotide sequences obtained from sequencing specific genetic library isolates can be subjected to further analysis in order to identify regions of interest in the genetic material. These regions of interest include additional open reading frames, promoter sequences, termination sequences, and the like. Isolated DNA can be characterized as being selected from the group consisting of:

(A) Isolated DNA selected from the group consisting of DNA having the nucleotide sequence which corresponds to, or substantially to, sequences described in SEQ ID NOS: 1, 3, 5, 7 and 9.

(B) Isolated double stranded DNA which hybridizes to isolated DNA of (a) above which encodes an enzyme or fragment thereof having carotenoid biosynthetic activity. Hybridization of such sequences may, for example, be carried out under stringent conditions (e.g., conditions represented by a wash stringency of 0.3M NaCl, 0.03M sodium citrate, 0.1% SDS at 70° C. to DNA of (a) above) in a standard in situ hybridization assay. See J. Sambrook et al., *Molecular Cloning: A Laboratory Manual* (2d Ed.), Cold Spring Harbor Laboratory, Cold Spring Harbor, N.Y. (1989). In general, such sequences will be at least 95% homologous, often at least 98% homologous, and even at least 99% homologous with the sequences of (a) above.

(C) Isolated DNA homologous to isolated double stranded DNA of (a) and (b) above. Homology relates to substantial or complete identity of nucleic acid sequences; and two nucleic acid fragments are homologous if they are capable of hybridizing to one another under hybridization conditions described in Maniatis et al., *Molecular Cloning: A Laboratory Manual*, Cold Spring Harbor Laboratory, Cold Spring Harbor, N.Y., pp. 320–323 (1982). Homologous sequences can be identified that contain less than about 5% base pair mismatches by using the following wash conditions: 2×SSC, 0.1% SDS, room temperature twice, 30 minutes each; then 2×SSC, room temperature twice, 10 minutes each. Homology can be assessed using computer programs such as DNASIS™ and PC Gene (LKB, Hitachi Corporation, Japan, and Intelligenetics, Palo Alto, Calif.) whereby the degree of homology is within the limits of homology considered significant by Bost et al., *Biochem. Biophys. Res. Commun.*, Vol. 128, pp. 1373–1380 (1985). More preferably, homologous nucleic acid strands contain less than 2% base pair mismatches, even more preferably less than 1% base pair mismatches. These degrees of homology can be selected by using more stringent wash conditions for identification of clones from gene libraries (or other sources of genetic material), as is well known in the art.

(D) Isolated DNA differing from the isolated DNA of (a), (b) and (c) above in nucleotide sequence due to the degeneracy of the genetic code, and which encodes either (i) a polypeptide identical to the polypeptides described in SEQ ID NOS: 2, 4, 6 and 8, or (ii) an enzyme or fragment thereof having carotenoid biosynthetic activity. For example, many of the nucleotide differences among the sequences are in the third "wobble" position of the codons such that the difference in nucleotide sequence does not necessarily lead to a difference in amino acid sequence. However, codon usage can have a large effect on the level of expression of a gene in a particular organism. Even genes encoding identical amino acid sequences can have vastly different levels of expression depending upon the codon preferences of the organism into which the genes are introduced.

Comparison of the 5' and 3' non-translated regions (NTRs) of the nucleotide sequences of the present invention with the known nucleotide tomato sequence (Ray et al., *Nucleic Acids Res.* Vol. 15, p. 10587 (1987)), reveals that these regions of the sequences of the present invention are much less conserved than the coding region. NTRs can be important in the expression of a gene product. For example, the NTRs can affect translatability or stability of mRNA. Genes with even closely related coding sequences have been observed to vary widely in the amount of protein product that is expressed from the gene. Comparison of the 5' NTRs of SEQ ID NOS: 1, 3, 5 and 7 show that the regions are highly conserved, and all start with the same nucleotide. This is consistent with the 5' sequence being the full length of the transcribed sequence. The tomato and other previously reported sequences are shorter than the sequences of the present invention, and may represent truncated versions of the transcripts. SEQ ID NO:9 is closely related to SEQ ID NO:5, but has a region of very little homology over the first 103 nucleotides of SEQ ID NO:9.

2. Polypeptides

The nucleotide sequences of the present invention are capable of encoding polypeptides having enzymatic activity for carotenoid biosynthesis. Such polypeptides have domains of amino acid sequences, including transit peptide regions and catalytic regions. The transit peptides which can be isolated are capable of directing proteins, or polypeptides which are fused to such transit peptides, to various subcellular locations (e.g., chloroplast membranes, chloroplast stroma and thylakoid membranes). The catalytic domains demonstrate enzymatic activity, can be isolated, and can be expressed in in vivo or in vitro systems. Comparison of the four complete Nicotiana phytoene synthase amino acid sequences of the present invention (i.e., SEQ ID NOS: 2, 4, 6 and 8) with the amino acid sequence of tomato PSY1 reveals sequence identities of about 85 percent to about 86 percent. The order of sequences from most to least identical to the tomato sequence is SEQ ID NOS: 6, 8, 4 and 2, with 358, 355, 353 and 351 identical amino acids, respectively. The tomato sequence has 413 total amino acids. SEQ ID NO:4 has 414 amino acids, while SEQ ID NOS: 2, 6 and 8 have 411 amino acids. The largest amount of sequence divergence is seen in the first approximately 100 amino acids in the region predicted to be a chloroplast transit peptide sequence, and at the carboxy-termini of the proteins. Variations in the chloroplast transit peptide sequence could possibly result in differences in the efficiency of transport of the preproteins into the chloroplasts.

A polypeptide derivative of a carotenoid biosynthetic enzyme can differ in length from the natural enzyme, but typically contains numerous amino acids from the natural enzyme in the same primary order as found in that enzyme as obtained from a natural source. Such a polypeptide molecule has substantially the same full length amino acid sequence as the natural enzyme but possesses minor amino acid substitutions that do not substantially affect the ability of that derivative to cause biosynthesis of carotenoids. Derivatives include glycosylated forms, aggregative conjugates with other enzyme molecules and covalent conjugates with unrelated chemical moieties. Covalent derivatives are prepared by linkage of functionalities to groups which are found in the enzyme amino acid chain or at the N- or C-terminal residue by means known in the art.

Isolated nucleotide sequences encoding biosynthetic enzymes can be used to produce purified enzymes or derivatives thereof by either recombinant DNA methodology or by in vitro polypeptide synthesis techniques. Purified and isolated polypeptides or nucleotide sequences are present in the substantial absence of other biological macromolecules of the same type.

3. Recombinant Techniques

Biosynthetic enzymes and polypeptide derivatives of those enzymes can be expressed by recombinant techniques when a DNA sequence encoding the relevant molecule is functionally inserted into a vector (e.g., in proper reading frame and orientation, as is well understood by those skilled in the art). Typically, the relevant gene will be inserted downstream from a promoter and will be followed by a stop codon, although production as a hybrid protein followed by cleavage may be used, if desired. In general, host-cell-specific sequences improving the production yield of enzyme and enzyme derivatives can be used, and appropriate control sequences (e.g., enhancer sequences, polyadenylation sequences, and ribosome binding sites) can be added to the expression vector.

A genetic construct can be prepared and used to transform plant cells. The transformed plant cells may be cells in culture, may be present as a disorganized mass in callus, leaf explants, or shoot cultures, or may be a post-transformation differentiated plant or plant part, such as seeds, leaves, roots, or the like. The foreign construct normally is present in all or substantially all of the cells of the plant tissue, but expression may be limited to particular cells or particular times in the development of the plant. The foreign construct normally includes transcriptional and translational initiation and termination signals, with the initiation signals 5' to the gene of interest and the termination signals 3' to the gene of interest.

The transcriptional initiation region which includes an RNA polymerase binding site (i.e., promoter) may be native to the host or may be derived from an alternative source, where the region is functional in the plant host. Other sources include the nos Agrobacterium T-DNA genes.

The transcriptional initiation regions may include, in addition to the RNA polymerase binding site, regions providing for regulation of transcription. The 3' termination region may be derived from the same gene as the transcriptional initiation region or from a different gene. For example, where the gene of interest has a transcriptional termination region functional in the host species, that region may be retained with the gene.

An example of an expression cassette is one that includes: a) the transcriptional initiation region, b) the biosynthetic enzyme gene under the transcriptional regulatory control of the transcription initiation region, c) the translation initiation codon, d) the coding sequence of the gene with or without introns, and e) the translational stop codon, followed by f) the transcriptional termination region. The transcriptional termination region includes the terminator, and may include a polyadenylation signal sequence and other sequences associated with transcriptional termination. The direction is 5' to 3' in the direction of transcription.

Where the expression product of the gene is to be located in a subcellular or extracellular compartment other than the cytoplasm, the gene usually is constructed to include particular amino acid sequences which result in translocation of the product to a particular site, which may be an organelle, such as the chloroplast, mitochondrion or nucleus, the cell plasma membrane, or may be secreted into the external environment of the cell. Various secretory leaders, membrane integrator sequences, and translocation sequences for directing the peptide expression product to a particular site are described in the literature. See, for example, Cashmore et al., *Biotechnology*, Vol. 3, pp. 803–808 (1985), and Wickner and Lodish, *Science*, Vol. 230, pp. 400–407 (1985).

The expression cassette normally is carried on a vector having at least one replication system. For convenience, it is common to have a replication system function in *E. coli* such as ColE1, pSC101, pACYC184, or the like. In this manner, at each stage after each manipulation, the resulting construct may be cloned, sequenced, and the correctness of the manipulation determined.

In addition to the replication system, there frequently is at least one selectable marker present, which may be useful in one or more hosts, or different markers for individual hosts. That is, one marker may be employed for selection in a prokaryotic host, while another marker may be employed for selection in a eukaryotic host, particularly the plant species host. The markers may be protection against a biocide, such as antibiotics, toxins, heavy metals, or the like; or complementation, imparting prototropy to an auxotrophic host.

The various fragments comprising the various constructs, expression cassettes, markers, and the like may be introduced consecutively by restriction enzyme cleavage of an appropriate replication system, and insertion of the particular construct or fragment into the available sites. After ligation and cloning, the vector may be isolated for further manipulation. All of these techniques are amply exemplified in the literature and find particular exemplification in Sambrook et al., *Molecular Cloning: A Laboratory Manual*, second edition, Cold Spring Harbor Laboratory, Cold Spring Harbor, N.Y., (1989).

Figure 2:
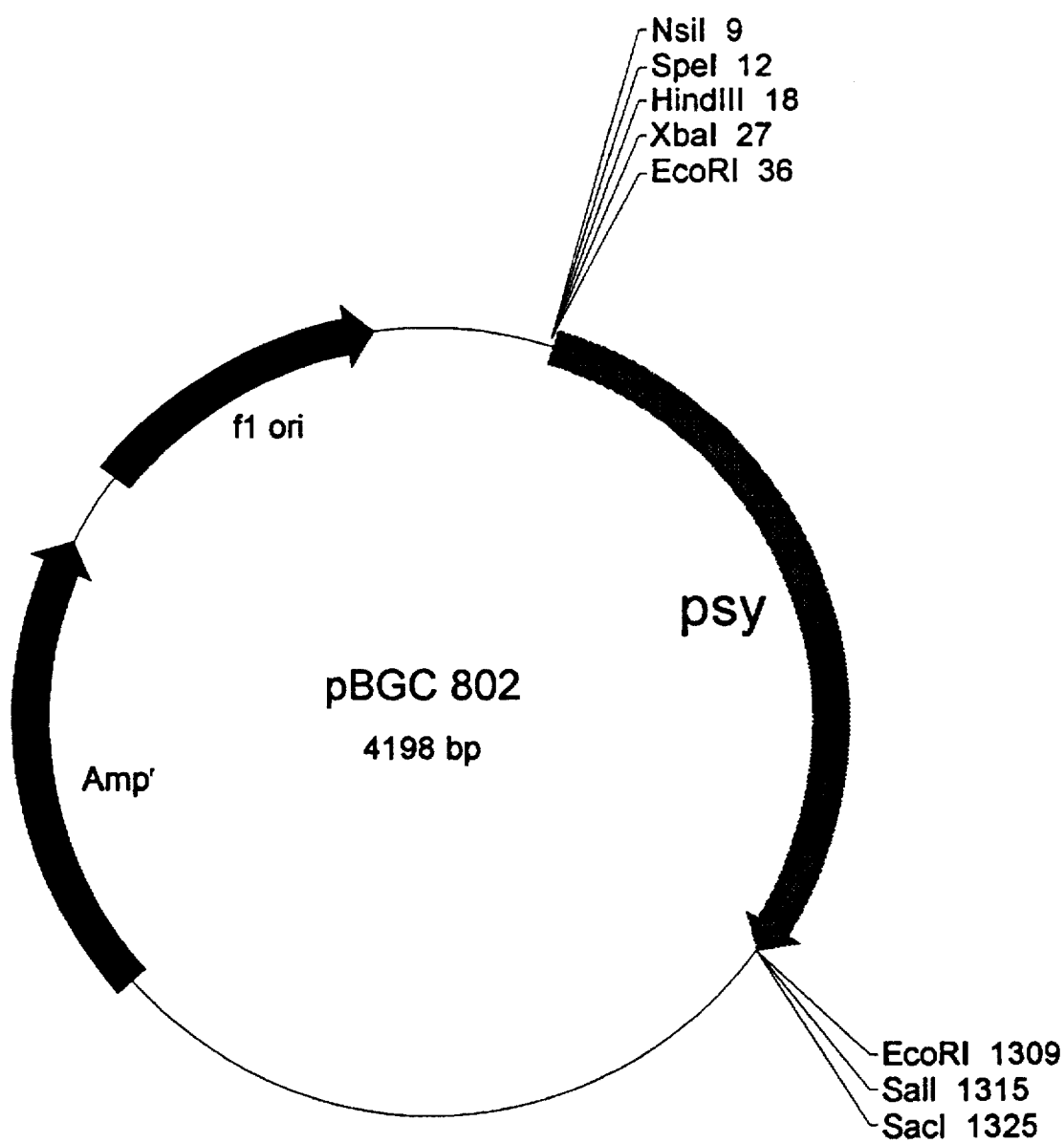
FIG. 2 is a map of the plasmid pBGC802, which contains the *N. benthamiana* phytoene synthase coding sequence from SEQ ID NO:3 as an EcoRI fragment cloned into pGEM9Zf(−) (Promega Corp.).

As an illustration of a specific example, the phytoene synthase coding region can be excised from plasmid pBGC802 (see FIG. 2) by digestion with XbaI and SalI. The insert can be separated from the vector on a 1% agarose gel, the band excised from the gel, and the DNA isolated. A T-DNA cloning can likewise be prepared by digestion with XbaI and XhoI. The insert then can be ligated into the vector using T4 DNA ligase and transformed into *E. coli.*

Once the vector is completed, the vector may be introduced into plant cells. Techniques for transforming plant cells include microinjection, particle bombardment, direct DNA uptake, such as using polyethylene glycol, electroporation, viral infection, and transformation with Agrobacterium. See, for example, D'Halluin et al., *The Plant Cell* Vol. 4, pp. 1495–1505 (1992), Tomes et al., *Plant Mol. Biol.* Vol. 14, pp. 261–268, Zhu et al., *Plant Cell, Tissue, and Organ Culture* Vol. 22, pp. 135–145 for representative techniques.

As an illustration of a specific example, the above-mentioned plasmid DNA can be propagated in, then isolated from *E. coli*, then introduced into Agrobacterium tumefaciens LBA4404 (a bacterial strain widely available to plant biotechnologists) by electroporation. Transformants can be selected on agar plates containing 25 μg/ml kanamycin.

Leaf disc transformation can be used to introduce the T-DNA into *Nicotiana tabacum* and *Nicotiana benthamiana* using standard protocols (e.g., Fitzmaurice et al., Plant Molecular Biology 20 (1992) 177–198). Transformed shoots can be selected on medium containing kanamycin. Shoots can then be excised and placed in rooting medium containing kanamycin. When roots first appear, plantlets can be transferred into soil and grown to maturity.

The nucleotide sequence encoding a given enzyme can be functionally inserted into plants or transiently expressed by virus-based gene delivery systems. Such a system is described in European Patent Application Nos. 67,553, 194,809 and 406,267, PCT WO 93/20217 and U.S. Pat. Nos. 5,304,731 and 5,316,931; which are incorporated herein in their entirety by reference. Such a system involves delivery of a selected nucleotide sequence as part of, or in conjunction with, a self-replicating DNA or RNA molecule (e.g., a virus), such that the exogenous gene is replicated and expressed during the course of replication and expression of viral or virus-based nucleic acids and proteins. Such gene delivery systems, in addition to enhancing gene "copy number" through the replicative potential of the given virus or virus-based nucleic acids, facilitate the timed delivery of such exogenous genes at the desired state of host development.

An exemplary virus-based gene delivery system employs tobacco mosaic virus. A DNA copy of the virus has a DNA sequence of the present invention inserted therein using conventional techniques of molecular cloning. The cloned DNA copy of the resulting viral vector then is transcribed to produce an RNA. The resulting RNA transcript vector then can be used to inoculate a grown *Nicotiana benthamiana* or *Nicotiana tabacum* plant by applying that RNA transcript onto a carborundum-dusted leaf in the direction of the leaf tip with a gloved finger. The plant so inoculated and infected with the virus vector is allowed to continue growing for about 3 weeks and then is harvested. The harvested plant can be extracted immediately or frozen for storage purposes. This infected plant material, or the vector virions isolated from it, can then be used for the inoculation of a multiplicity of plants for purposes of significantly amplifying the delivered gene or gene product. In order to accomplish this, the leaf tissue so collected is mixed with a 10 mM phosphate buffer (pH 7.5) at a ratio of about 1:10 (w/v). The mixture is macerated using a high speed blender, and centrifuged so as to obtain a liquid inoculum. The inoculum then can be applied to a growing plant, such as a tobacco plant, by applying the inoculum to injured (e.g., lacerated) regions of that plant. For example, the upper most leaves of the growing plant can be cut using an inoculum-wetted cutting blade (e.g., by spray nozzles located in the cutting blade); or the inoculum can be sprayed onto a specific region of one leaf of the plant as a high pressure spray. The plant is allowed to continue growing in order that the viral vector can systemically infect the plant. At a desired stage of infection, the plant is harvested.

As an illustration of a specific example of the use of a viral vector, one can also deliver an antisense copy of the phytoene synthase sequence for purposes of inhibiting phytoene synthase gene expression. In this case the phytoene synthase gene can be transiently expressed in a plant using a virus-based gene delivery system. For example, the plasmid pBGC802 (see FIG. 2) can be digested with SalI and XbaI, and the insert fragment containing phytoene synthase separated from the vector fragment on an agarose gel. The fragment can be excised from the gel, and the DNA purified. The viral vector, pTTO1A (Kumagai, et al., *Proc Natl Acad Sci*, Vol. 92, pp. 1679–1683 (1995)), can likewise be prepared by digestion with XhoI and AvrII with separation on an agarose gel. The vector fragment can be excised from the gel, and the DNA purified. The viral vector and the phytoene synthase insert can be ligated using T4 DNA ligase under standard conditions and transformed into *E. coli*.

A transcript of the viral vector containing phytoene synthase in the antisense orientation can be created from the SP6 RNA polymerase promoter site contained in the vector using SP6 RNA polymerase. The infectious transcript can then be inoculated onto plants.

The following examples are provided in order to further illustrate the invention but should not be construed as limiting the scope thereof. Unless otherwise noted, all parts and percentages are by weight.

EXAMPLE 1

Isolation of Phytoene Synthase Genes

Isolation of genes encoding phytoene synthase was carried out as follows.

1. Amplification of the central portion of a *Nicotiana tabacum* phytoene synthase gene.

Oligonucleotide primers for polymerase chain reaction (PCR) amplification were designed based upon the tomato psy DNA sequence (e.g. Ray et al., *Nucl Acids Res*, Vol. 15, p. 10587 (1987)). Appropriate primers were synthesized from these sequences on a DNA synthesizer or were obtained from commercial sources.

A tobacco cDNA library was used as the template for a PCR amplification. A 50 μl reaction was assembled with a final composition of 20 mM Tris-HCl (pH 8.4), 50 mM KCl, 2.5 mM, 100 μg/ml BSA, 200 nM Primer PSYY154 (5'-TAT GTA TGG TGC AGA AGA ACA GAT-3') (SEQ ID NO:10), 200 nM Primer PSD298 (5'-AGT CGA CTC TTC CTC TTC TGG CAT C-3') (SEQ ID NO:11), 0.2 mM each dATP, dCTP, dGTP and dTTP, 5 ng tobacco cDNA library DNA, and 0.04 U/μl Taq DNA Polymerase. Amplification was in a DNA thermocycler with 35 cycles of 1 min at 94° C., 1 min at 50° C., and 1 min at 72° C.

The resulting PCR product was cloned using the pCRII vector (Invitrogen Corporation, San Diego, Calif.). Clones were subjected to DNA sequence analysis using standard methods. The sequence was examined for homology with the published phytoene synthase gene sequences. Clones were detected exhibiting nucleotide homology with the coding region of tomato phytoene synthase. The DNA sequence of this tobacco phytoene synthase fragment was used to design oligonucleotide primers for further amplifications.

2. Isolation of RNA from *Nicotiana benthamiana* and *Nicotiana tabacum*:

About 200 mg of plant leaf tissue was harvested and frozen in liquid nitrogen. The tissue was ground to a powder with a mortar and pestle and then transferred to a glass homogenizer. One ml of AGRIsol (Biogentex, Houston, Tex.) was added to the tissue, and the mixture was homogenized. The homogenate was transferred to a microfuge tube and 100 μl of chloroform was introduced into the tube. The mixture was shaken by hand for 20 sec. Then, the mixture was incubated for 5 min on ice, and centrifuged for 10 min at 10,000×g at 4° C. The aqueous phase of the centrifuged mixture was transferred to a separate tube, and the RNA was precipitated from that phase by addition of 1 volume of isopropanol. After incubation on ice for 5 min that sample was centrifuged for 10 min at 10,000×g at 4° C. The resulting pellet was collected and washed twice with ethanol (75% in water). The pellet was air-dried for about 15 min. The pellet was resuspended in 1 ml RNase-free dH$_2$O. The RNA concentration was calculated by determining the OD$_{260}$nm (1 OD$_{260}$nm=40 μg/ml).

3. 3' RACE amplification of phytoene synthase:

About 200 ng of total RNA was heated with 10 pg of Adapter Primer (Gibco BRL, 5'-GGC CAC GCG TCG ACT AGT AC(T)$_{17}$-3' (SEQ ID NO:12) for 10 min at 65° C. and then chilled 2 min on ice. The reaction mixture was made up to 20 μl total volume with final concentrations of 20 mM Tris-HCl (pH 8.4), 50 mM KCl, 2.5 mM, 100 μg/ml BSA, 10 mM DTT, 500 nM Adapter Primer and 0.5 mM each dATP, dCTP, dGTP and dTTP. The mixture was equilibrated 2 min at 42° C. 200 units of reverse transcriptase were added and the mixture incubated 30 min at 42° C. Two units of *E. coli* RNase H were added and the mixture incubated 10 min at 42° C. to yield the first strand cDNA.

The first strand cDNA was directly amplified by the PCR method. A 50 μl reaction was assembled with a final composition of 20 mM Tris-HCl (pH 8.4), 50 mM KCl, 2.5 mM, 100 μg/ml BSA, 200 nM Primer PSYY154 (5'-TAT GTA TGG TGC AGA AGA ACA GAT-3') (SEQ ID NO:10), 200 nM Universal Amplification Primer (Gibco BRL, Gaithersburg, Md.), 0.2 mM each dATP, dCTP, dGTP and dTTP, and 0.04 U/μl Taq DNA Polymerase. Amplification was in a DNA thermocycler with 1 cycle of 2 min at 94° C., 30 cycles of 1 min at 94° C., 1 min at 50° C., 2 min at 72° C., and 1 cycle of 15 min at 72° C. Nested amplification was performed in a 50 μl reaction with a final composition of 10 mM Tris-HCl (pH 8.3), 50 mM KCl, 1.5 mM MgCl$_2$, 0.001% (w/v) gelatin, 0.2 mM each dATP, dCTP, dGTP and dTTP, 200 nM Universal Amplification Primer, 200 nM primer WPF5 (5'-AGC GGG CGA CCA TTT GAT ATG CTC G-3') (SEQ ID NO:13), 1 μl PCR products (above), and 0.025 U/μl Taq DNA Polymerase. Amplification was in a DNA thermocycler with 1 cycle of 2 min at 94° C., 30 cycles of 1 min at 94° C., 1 min at 55° C., 2 min at 72° C., and 1 cycle of 15 min at 72° C.

4. Southern Analysis of PCR Products:

Nested PCR 3' RACE products were analyzed by separation on a 1% agarose gel in TBE buffer (44.5 mM Tris-borate, 44.5 mM boric acid 1 mM EDTA). The PCR products in the gel were denatured by treatment for 20 min in 1.5M NaCl, 0.5N NaOH and neutralized by soaking in several volumes of 1.5M NaCl, 1M Tris-HCl (pH 8.0). The PCR products were transferred to a nylon membrane and were UV-crosslinked.

Hybridization and detection of phytoene synthase homologous nucleotide sequences were performed using a chemiluminescent system. The membrane was prehybridized for 1 hr at 60° C. in 10 ml hybridization solution (5× SSC, 1× Blocking solution 0.1% N-laurylsarcosinate, 0.02% sodium dodecylsulfate (SDS); 10× Blocking solution is 10% (w/v) Blocking Reagent (Boehringer Mannheim Biochemicals, Indianapolis, Ind.) in 100 mM maleic acid at pH 7.5, 150 mM NaCl). Incubations were in a rotating bottle hybridization incubator. Heat-denatured (5 min at 100° C.) probe was added to the prehybridization mixture at a final concentration of 1.25 ng/ml, and incubation of the resulting mixture was continued 4–16 hr at 60° C. The membrane was washed twice for 5 min in 2× SSC, 0.1% SDS at room temperature, and twice for 15 min in 0.1× SSC, 0.1% SDS at 60° C. For chemiluminescent detection the membrane was rinsed in 100 mM maleic acid, 150 mM NaCl, and incubated for 30 min at room temperature in 1× Blocking solution. Alkaline phosphatase-conjugated anti-digoxigenin Fab fragments were added (1:10,000 dilution), and incubation was continued for 30 min at room temperature. The membrane was washed twice for 15 min in 100 mM maleic acid, 150 mM NaCl, at room temperature. The membrane was equilibrated for 2 min in 100 mM Tris-HCl (pH 9.5), 100 mM NaCl, 50 mM MgCl$_2$. The membrane was placed on a sheet of clear acetate film and Lumi-Phos 530 (Boehringer Mannheim Biochemicals, Indianapolis, Ind.) was added on the DNA side of the membrane. Another sheet of acetate film was used to cover the membrane, and the membrane was exposed to X-ray film. Positive signals on the X-ray film indicated the presence of PCR products containing phytoene synthase homologous gene sequences.

Probe for the phytoene synthase nucleotide sequence was generated by random-primed labeling of a double stranded cDNA of tomato phytoene synthase with digoxigenin-dUTP according to standard techniques. The probe concentration was determined by comparison with a dilution series of a known standard on a nylon membrane and detection by chemiluminescence as above. Cloning of the 3' RACE products:

The nested PCR 3' RACE products of phytoene synthase gene sequences were cloned using the pCRII vector (Invitrogen Corporation, San Diego, Calif.).

Clones were screened by digestion with EcoRI to liberate the insert, separation on an agarose gel, transfer to a nylon membrane, and hybridization and detection as described above. Clones exhibiting a positive hybridization signal were subjected to DNA sequence analysis using standard methods.

The sequence was examined for homology with the published phytoene synthase nucleotide sequences. Clones were detected exhibiting nucleotide homology with the coding region of the tomato phytoene synthase gene. Many of the nucleotide changes were in the third position of the codons (the wobble position) and did not change the encoded amino acid. The regions of least homology were at the 3' end.

5. 5' RACE amplification of phytoene synthase

5' RACE (Gibco BRL) was used to generate 5' RACE products of phytoene synthase gene sequences. About 200 ng of total RNA from *Nicotiana benthamiana* or *Nicotiana tabacum* was heated with 2 pg primer WPF6 (5'-CAT CAA CCC AAC CGT ACC AGC AAC G-3') (SEQ ID NO:14) for 5 min at 70° C. and then chilled 2 min on ice. The reaction mixture was made up to 20 μl total volume with final concentrations of 20 mM Tris-HCl (pH 8.4), 50 mM KCl, 2.5 mM, 100 μg/ml BSA, 10 mM DTT, 100 nM Primer WPF6 and 0.5 mM each dATP, dCTP, dGTP and dTTP. The mixture was equilibrated 2 min at 42° C. 200 units of reverse transcriptase were added and the mixture incubated 30 min at 42° C. The mixture was incubated 15 min at 70° C. to inactivate the reverse transcriptase. The mixture was incubated 5 min at 55° C., two units of *E. coli* RNase H were added and the mixture incubated 10 min at 55° C. to yield the first strand cDNA. Excess primer was removed by purification with a Gibco BRL GlassMAX™ spun column. To the first strand cDNA reaction 95 µl of 6M NaI was added at room temperature. The mixture was transferred to a GlassMAX™ column and centrifuged 20 sec at 16,000×g. The column was washed three times with 400 µl aliquots of ice cold wash buffer with 20 sec centrifugations. The column then was washed with a 400 µl aliquot of cold 70% ethanol and a 20 sec centrifugation. The cDNA was eluted with 50 µl of 65° C. dH$_2$O.

A poly (dC) tail was added to the cDNA. Ten µl of purified cDNA mixture plus 6 µl of dH$_2$O was incubated 5 min at 70° C. then chilled on ice. The cDNA was assembled into a 20 µl reaction containing 10 mM Tris-HCl (pH 8.4), 25 mM KCl, 1.25 mM MgCl$_2$, 50 µg/ml BSA, 0.2 mM dCTP and 0.5 units/µl terminal deoxynucleotidyl transferase. After incubation for 10 min at 37° C., the terminal deoxynucleotidyl transferase was heat inactivated 10 min at 70° C.

The dC-tailed cDNA was amplified by the Hot Start PCR method. A 45 µl reaction was assembled with 10 µl of first strand cDNA mixture, buffer, nucleotides and primers. An AmpliWax PCR Gem (Perkin Elmer Cetus, Norwalk, Conn.) was added and the reaction incubated 5 min at 80° C. followed by cooling to 25° C. Five µl of reaction buffer containing 0.25 U Taq DNA Polymerase was added on top of the wax. The final composition of the reaction was 10 mM Tris-HCl (pH 8.3), 50 mM KCl, 1.5 mM MgCl$_2$, 0.001% (w/v) gelatin, 0.2 mM each dATP, dCTP, dGTP and dTTP, 400 nM primer WPF7 (5'-ACT TCC TCA AGT CCA TAC GCA TTC C-3') (SEQ ID NO:15) and 400 nM Anchor Primer (Gibco BRL, Gaithersburg, Md.). Amplification was in a DNA thermocycler with 1 cycle of 2 min at 94° C., 35 cycles of 10 sec at 94° C., 15 sec at 57° C., 90 sec at 72° C., and 1 cycle of 5 min at 72° C. To get rid of excess primers, the PCR reaction products were purified using a GlassMAX column (Gibco BRL).

Nested amplification was performed using the Hot Start PCR method as above in a 50 µl reaction with a final composition of 10 mM Tris-HCl (pH 8.3), 50 mM KCl, 1.5 mM MgCl$_2$, 0.001% (w/v) gelatin, 0.2 mM each dATP, dCTP, dGTP and dTTP, 200 nM Universal Amplification Primer, 200 nM primer WPF38 (5'-CTA CAC CTA TCA TAT GCT TCA C-3') (SEQ ID NO:16), 0.025% of the purified PCR products (above), and 0.025 U/µl Taq DNA Polymerase. Amplification was in a DNA thermocycler with 1 cycle of 2 min at 94° C., 25 cycles of 10 sec at 94° C., 15 sec at 55° C., 90 sec at 72° C., and 1 cycle of 5 min at 72° C.

6. Cloning of PCR Products:

Nested PCR 5' RACE products of phytoene synthase gene sequences were analyzed and cloned as described previously with reference to the 3' RACE products.

7. Amplification of the full-length coding region of phytoene synthase:

In many cases gene families are expressed in Nicotiana. Often such genes will be highly homologous, and, as such, PCR strategies based upon primer sequences derived from conserved regions of a gene of interest are expected to amplify mRNA from each of the expressed genes.

The multiple nature of some genetic loci in Nicotiana is of particular concern when cloning genes via 5' RACE and 3' RACE techniques. When assembling parts of the genetic sequence to create intact genes, the DNA sequences of the same gene family member must be matched to avoid the generation of chimeric genes. Alternatively, examination of the DNA sequence of the RACE products can allow the design of primers for the start and stop codons of the gene facilitating amplification of entire coding regions from RNA obviating the possibility of assembly of chimeras.

The first strand cDNA was generated from total RNA from *N. benthamiana* or *N. tabacum*. In a 15 µl reaction 0.5 µg oligo (dT) (GibcoBRL) was added to 2 µg total RNA. The mixture was heated 10 min at 70° C., then chilled on ice for 1 min. The reaction mixture was made up to 20 µl total volume with final concentrations of 20 mM Tris-HCl (pH 8.4), 50 mM KCl, 2.5 mM, 100 µg/ml BSA, 10 mM DTT, 0.5 mM each dATP, dCTP, dGTP and dTTP. Reverse transcriptase (200 units) was added and the mixture was incubated 10 min at 25° C., then 50 min at 42° C. The mixture was incubated 15 min at 70° C. to stop the reaction. The mixture was equilibrated to 37° C., two units of *E. coli* RNase H were added and the mixture incubated 20 min at 37° C. to yield the first strand cDNA.

The first strand cDNA was amplified by the Hot Start PCR method. A 45 µl reaction was assembled with 10 µl of first strand cDNA mixture, buffer, nucleotides and primers. An AmpliWax PCR Gem (Perkin Elmer Cetus, Norwalk, Conn.) was added and the reaction incubated 5 min at 80° C. followed by cooling to 25° C. Five µl of reaction buffer containing 0.25 U Taq DNA Polymerase was added on top of the wax. The final composition of the reaction was 10 mM Tris-HCl (pH 8.3), 50 mM KCl, 1.5 mM MgCl$_2$, 0.001% (w/v) gelatin, 0.2 mM each dATP, dCTP, dGTP and dTTP, 400 nM primer WPF30 (5'-GCT CCA TAT GTC TGT TGC CTT GTT ATG G-3') (SEQ ID NO:17) and 400 nM Primer WPF31 (5'-TCG GAT CCC TAT GCC TTA GCT ATA GAG G-3') (SEQ ID NO:18) (for *N. benthamiana*) or primer WPF37 (5'-TCG GAT CCT TAG CTA GAG GTG ACA AGA G-3') (SEQ ID NO:19) (for *N. tabacum*). Amplification was in a DNA thermocycler with 1 cycle of 2 min at 94° C., 35 cycles of 10 sec at 94° C., 2 min at 65° C., and 1 cycle of 5 min at 72° C.

The full-length coding region PCR products of phytoene synthase were cloned using the pCRII vector (Invitrogen Corporation, San Diego, Calif.). Clones were screened by digestion with EcoRI to liberate the insert and separation on an agarose gel. Clones with appropriate inserts were subjected to DNA sequence analysis using standard methods.

DNA sequence was determined for the final constructs, and the sequence was translated to verify that the appropriate reading frame was maintained through the cloning steps. The plasmids were expressed in an in vitro translation system, and the protein products were examined by polyacrylamide gel electrophoresis (PAGE) to determine that an appropriately sized product was produced.

The phytoene synthase nucleic acid sequences provided from *Nicotiana benthamiana* have the nucleotide sequences specified by SEQ ID NOS: 1 and 3, and the amino acid sequences which have been deduced from those nucleotide sequences are specified in SEQ ID NOS: 2 and 4.

The phytoene synthase nucleic acid sequences provided from *Nicotiana tabacum* have the nucleotide sequences specified by SEQ ID NOS: 5 and 7, and the amino acid sequences which have been deduced from those nucleotide sequences are specified in SEQ ID NOS: 6 and 8. A 5' RACE product from N. tabacum having the same amino acid sequence as the overlapping portion of SEQ ID NO:5, but a partially different 5' non-translated region has the nucleotide sequence specified by SEQ ID NO:9.

EXAMPLE 2

Functional complementation by Nicotiana phytoene synthase of an Erwinia crt operon deleted for crtB A complementation assay like that described by Misawa et al. (*J Biochem*, Vol. 116, pp. 980–985 (1994)) was used to show that the Nicotiana psy encodes a functional phytoene synthase enzyme. A plasmid containing the *Erwinia herbicola* crt operon was modified by deletion of an EagI restriction fragment to yield pAPU211BZ that lacked expression of crtB and crtZ (see Hundle et al., *Mol Gen Genet*, Vol. 245, pp. 406–416 (1994)). *E. coli* containing the intact plasmid pAPU211 were yellow, but those containing pAPU211BZ were white. Hundle et al. also found that *E. coli* containing the plasmid with crtZ alone deleted (pAPU211Z) were orange. We reasoned that if we could complement the mutant plasmid pAPU211BZ by supplying the Nicotiana psy gene in appropriate form, the resulting *E. coli* should turn orange.

Misawa et al. demonstrated that various N-terminal deletions of tomato psy that removed portions or all of the Chloroplast Transit Peptide (CTP) sequence could be made to express phytoene synthase activity in *E. coli* when they were fused to the lacZ gene (the fusion provided a bacterial promoter and ribosome binding site). For example, a construction in which the first 109 amino acids were deleted from tomato psy was successfully used to complement the *E. uredovora* crtB deletion plasmid pACCAR25ΔcrtB and restore carotenoid synthesis. We generated a construction in which SEQ ID NO:5 as cloned into the pCRII vector was digested with SmaI to remove the first 109 amino acids and digested with XbaI at the 3' terminus. This fragment was cloned into the plasmid pPD112 (Dersch et al., *FEMS Microbiol Lett*, Vol. 123, pp. 19–26 (1994)) creating a fusion with the first 8 amino acids of lacZ under control of a T7 promoter sequence. This construct, pPD112Δpsy3, was introduced into *E. coli* BL21(DE3). Since the pPD112 has a pSC101 replicon, the compatible ColEI replicon-based pAPU211BZ could be introduced into the same strain. The BL21(DE3) provided a source of T7 RNA polymerase to allow expression of the SEQ ID NO:5-derived psy gene and so complementation of the crtB deletion. Colonies containing both plasmids turned orange, while colonies of a control strain (*E. coli* C600) that did not express T7 RNA polymerase (or psy) remained the normal white color of *E. coli*. This demonstrates that the psy sequence in SEQ ID NO:5 and, by inference, the highly homologous sequences in SEQ ID NOS: 1, 3 and 7, encode functional phytoene synthase.

EXAMPLE 3

Cloning of phytoene synthase sequences into a TMV-based viral vector

The phytoene synthase gene can be transiently expressed in a plant using a virus-based gene delivery system. For example, the plasmid pBGC803 (see FIG. 1) was digested with XhoI and SpeI, and the insert fragment containing phytoene synthase was separated from the vector fragment on an agarose gel. The fragment was excised from the gel, and the DNA was purified. The viral vector, pTTO1A (Kumagai, et al., *Proc Natl Acad Sci*, Vol. 92, pp. 1679–1683 (1995)), was prepared by digestion with XhoI and AvrII and separation on an agarose gel. The vector fragment was excised from the gel, and the DNA was purified. The viral vector and the phytoene synthase insert were ligated using T4 DNA ligase under standard conditions and transformed into *E. coli*.

A transcript of the viral vector containing the phytoene synthase gene was created from the SP6 RNA polymerase promoter site contained in the vector using SP6 RNA polymerase. The infectious transcript was inoculated onto plants.

The foregoing is illustrative of the present invention and is not to be construed as limiting thereof. The invention is defined by the following claims, with equivalents of the claims to be included therein.

That which is claimed is:

1. An isolated nucleic acid molecule encoding a polypeptide having enzymatic activity for producing phytoene, said molecule having a sequence selected from the group consisting of:
   (a) SEQ ID NO: 1, SEQ ID NO:3, SEQ ID NO:5, SEQ ID NO:7 and SEQ ID NO:9;
   (b) nucleotide sequences which encode a polypeptide having enzymatic activity for producing phytoene and which hybridize to sequences of (a) above under stringent conditions defined by a wash stringency of 0.3M NaCl, 0.03M sodium citrate, 0.1% SDS at 70° C.;
   (c) nucleotide sequences, which encode a polypeptide having enzymatic activity for producing phytoene and which differ from sequences of (a) and (b) due to the degeneracy of the genetic code.

2. An isolated nucleic acid molecule encoding a polypeptide which has enzymatic activity for producing phytoene, said polypeptide having an amino acid sequence selected from the group consisting of SEQ ID NO:2, SEQ ID NO:4, SEQ ID NO:6 and SEQ ID NO:8.

3. A nucleic acid molecule of claim 1 or 2 in the form of a DNA molecule.

4. A nucleic acid molecule of claim 3 isolated from a Nicotiana species.

\* \* \* \* \*

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 1795 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 362..1591

( x i ) SEQUENCE DESCRIPTION: SEQ ID NO:1:

```
AGAAGAAAAA  CAAAGGAACT  CCTTTGATTC  TTGAAGAGTA  TACAGTACCA  AACAAGCAAA      60

TTAAAGTGGC  TATACTTGAA  AAGCCATTGT  TACAAGAAAA  TTAAGAAGCC  AAGAAACTGG     120

TTATTTCTG   CTTGAGTTAG  AAAAAGCTGG  TTTGCTTTCT  TTGTGGATTC  TTATAATCTT     180

TTTTACATAA  GAGGAAGTGG  GTATTTCTTG  AAAGTGGATA  TAGAATCTAG  TGGGAATCTA     240

CTTGGAGTAA  ATTTATTTAT  TTTTTTATAA  ATTAAGGAGA  GGAGGGAAGG  AAACAGAAAA     300

CTGAAAGTAA  GACAAAAAAC  CTTGGAATTG  TTTAGACAA   CCAAGGTTTT  TCTTGCTCAG     360
```

-continued

| | | | | | | | | | | | | | | | | |
|---|---|---|---|---|---|---|---|---|---|---|---|---|---|---|---|---|
| A | ATG | TCT | GTT | GCC | TTG | TTA | TGG | GTT | GTT | TCA | CCT | TGT | GAG | GTC | TCA | 406 |
| | Met | Ser | Val | Ala | Leu | Leu | Trp | Val | Val | Ser | Pro | Cys | Glu | Val | Ser | |
| | 1 | | | | 5 | | | | | 10 | | | | | 15 | |

| AAT | GGG | ACA | GGA | TTC | TTG | GAT | TCA | ATT | CGG | GAG | GGA | AAC | CGG | GTT | TTT | 454 |
|---|---|---|---|---|---|---|---|---|---|---|---|---|---|---|---|---|
| Asn | Gly | Thr | Gly | Phe | Leu | Asp | Ser | Ile | Arg | Glu | Gly | Asn | Arg | Val | Phe | |
| | | | 20 | | | | | 25 | | | | | 30 | | | |

| GAT | TTG | TCG | AGG | TAT | AGA | AAT | TTA | GTG | TGC | AAT | GAG | AGG | AAC | AAG | AGA | 502 |
|---|---|---|---|---|---|---|---|---|---|---|---|---|---|---|---|---|
| Asp | Leu | Ser | Arg | Tyr | Arg | Asn | Leu | Val | Cys | Asn | Glu | Arg | Asn | Lys | Arg | |
| | | | 35 | | | | | 40 | | | | | 45 | | | |

| GGT | GGG | AAA | CAA | AGG | TGG | AAT | TTT | GGT | TCT | GTA | AGG | TCT | GCT | ATG | GTG | 550 |
|---|---|---|---|---|---|---|---|---|---|---|---|---|---|---|---|---|
| Gly | Gly | Lys | Gln | Arg | Trp | Asn | Phe | Gly | Ser | Val | Arg | Ser | Ala | Met | Val | |
| | | | 50 | | | | | 55 | | | | | 60 | | | |

| GCT | ACA | CCG | GCG | GGA | GAA | ATG | GCG | ACG | ATG | ACA | TCA | GAA | CAG | ATG | GTT | 598 |
|---|---|---|---|---|---|---|---|---|---|---|---|---|---|---|---|---|
| Ala | Thr | Pro | Ala | Gly | Glu | Met | Ala | Thr | Met | Thr | Ser | Glu | Gln | Met | Val | |
| | 65 | | | | | 70 | | | | | 75 | | | | | |

| TAT | GAT | GTG | GTT | TTA | AAA | CAA | GCA | GCT | TTA | GTG | AAG | AGG | CAG | TTG | AGA | 646 |
|---|---|---|---|---|---|---|---|---|---|---|---|---|---|---|---|---|
| Tyr | Asp | Val | Val | Leu | Lys | Gln | Ala | Ala | Leu | Val | Lys | Arg | Gln | Leu | Arg | |
| 80 | | | | | 85 | | | | | 90 | | | | | 95 | |

| TCT | ACT | GAT | GAT | TTA | GAA | GTG | AAG | CCG | GAG | ATC | CCT | CTC | CAG | GCA | AAT | 694 |
|---|---|---|---|---|---|---|---|---|---|---|---|---|---|---|---|---|
| Ser | Thr | Asp | Asp | Leu | Glu | Val | Lys | Pro | Glu | Ile | Pro | Leu | Gln | Ala | Asn | |
| | | | | 100 | | | | | 105 | | | | | 110 | | |

| TTG | AGC | TTG | TTG | AGT | GAA | GCA | TAT | GAT | AGG | TGT | AGT | GAA | GTA | TGT | GCA | 742 |
|---|---|---|---|---|---|---|---|---|---|---|---|---|---|---|---|---|
| Leu | Ser | Leu | Leu | Ser | Glu | Ala | Tyr | Asp | Arg | Cys | Ser | Glu | Val | Cys | Ala | |
| | | | 115 | | | | | 120 | | | | | 125 | | | |

| GAG | TAT | GCA | AAG | ACA | TTT | TAC | TTA | GGA | ACC | ATG | CTA | ATG | ACT | CCA | GAG | 790 |
|---|---|---|---|---|---|---|---|---|---|---|---|---|---|---|---|---|
| Glu | Tyr | Ala | Lys | Thr | Phe | Tyr | Leu | Gly | Thr | Met | Leu | Met | Thr | Pro | Glu | |
| | | 130 | | | | | 135 | | | | | 140 | | | | |

| AGA | AGA | AGG | GCT | ATT | TGG | GCA | ATA | TAT | GTA | TGG | TGC | AGG | AGA | ACA | GAT | 838 |
|---|---|---|---|---|---|---|---|---|---|---|---|---|---|---|---|---|
| Arg | Arg | Arg | Ala | Ile | Trp | Ala | Ile | Tyr | Val | Trp | Cys | Arg | Arg | Thr | Asp | |
| 145 | | | | | 150 | | | | | 155 | | | | | | |

| GAA | CTT | GTT | GAT | GGC | CCG | AAT | GCA | TCC | CAT | ATT | ACC | CCA | CAA | GGC | TTA | 886 |
|---|---|---|---|---|---|---|---|---|---|---|---|---|---|---|---|---|
| Glu | Leu | Val | Asp | Gly | Pro | Asn | Ala | Ser | His | Ile | Thr | Pro | Gln | Gly | Leu | |
| 160 | | | | | 165 | | | | | 170 | | | | | 175 | |

| GAT | AGG | TGG | GAA | GAC | CTG | CTG | GAA | GAT | GTT | TTC | AGT | GGG | CGG | CCA | TTT | 934 |
|---|---|---|---|---|---|---|---|---|---|---|---|---|---|---|---|---|
| Asp | Arg | Trp | Glu | Asp | Leu | Leu | Glu | Asp | Val | Phe | Ser | Gly | Arg | Pro | Phe | |
| | | | | 180 | | | | | 185 | | | | | 190 | | |

| GAT | ATG | CTC | GAT | GCT | GCT | TTG | TCC | GAT | ACT | GTT | TCC | AAG | TTT | CCA | GTT | 982 |
|---|---|---|---|---|---|---|---|---|---|---|---|---|---|---|---|---|
| Asp | Met | Leu | Asp | Ala | Ala | Leu | Ser | Asp | Thr | Val | Ser | Lys | Phe | Pro | Val | |
| | | | 195 | | | | | 200 | | | | | 205 | | | |

| GAT | ATT | CAG | CCA | TTC | AGA | GAT | ATG | ATT | GAA | GGA | ATG | CGT | ATG | GAC | TTG | 1030 |
|---|---|---|---|---|---|---|---|---|---|---|---|---|---|---|---|---|
| Asp | Ile | Gln | Pro | Phe | Arg | Asp | Met | Ile | Glu | Gly | Met | Arg | Met | Asp | Leu | |
| | | 210 | | | | | 215 | | | | | 220 | | | | |

| AGG | AAG | TCA | AGA | TAC | AGA | AAC | TTT | GAT | GAG | CTA | TAC | CTA | TAT | TGT | TAT | 1078 |
|---|---|---|---|---|---|---|---|---|---|---|---|---|---|---|---|---|
| Arg | Lys | Ser | Arg | Tyr | Arg | Asn | Phe | Asp | Glu | Leu | Tyr | Leu | Tyr | Cys | Tyr | |
| 225 | | | | | 230 | | | | | 235 | | | | | | |

| TAC | GTT | GCT | GGT | ACG | GTT | GGG | TTG | ATG | AGT | GTT | CCA | ATT | ATG | GGT | ATT | 1126 |
|---|---|---|---|---|---|---|---|---|---|---|---|---|---|---|---|---|
| Tyr | Val | Ala | Gly | Thr | Val | Gly | Leu | Met | Ser | Val | Pro | Ile | Met | Gly | Ile | |
| 240 | | | | | 245 | | | | | 250 | | | | | 255 | |

| GCA | CCT | GAT | TCA | AAG | GCA | ACA | ACA | GAG | AAT | GTA | TAT | AAT | GCA | GCT | TTG | 1174 |
|---|---|---|---|---|---|---|---|---|---|---|---|---|---|---|---|---|
| Ala | Pro | Asp | Ser | Lys | Ala | Thr | Thr | Glu | Asn | Val | Tyr | Asn | Ala | Ala | Leu | |
| | | | | 260 | | | | | 265 | | | | | 270 | | |

| GCT | TTG | GGT | ATA | GCA | AAT | CAA | CTA | ACA | AAC | ATA | CTC | AGA | GAT | GTC | GGA | 1222 |
|---|---|---|---|---|---|---|---|---|---|---|---|---|---|---|---|---|
| Ala | Leu | Gly | Ile | Ala | Asn | Gln | Leu | Thr | Asn | Ile | Leu | Arg | Asp | Val | Gly | |
| | | | 275 | | | | | 280 | | | | | 285 | | | |

| GAA | GAT | GCC | AGA | AGA | GGA | AGA | GTC | TAC | TTA | CCT | CAA | GAT | GAA | TTA | GCA | 1270 |
|---|---|---|---|---|---|---|---|---|---|---|---|---|---|---|---|---|
| Glu | Asp | Ala | Arg | Arg | Gly | Arg | Val | Tyr | Leu | Pro | Gln | Asp | Glu | Leu | Ala | |
| | | 290 | | | | | 295 | | | | | 300 | | | | |

| CAT | GCA | GGT | CTC | TCC | GAC | GAT | GAC | ATA | TTC | GCT | GGA | AAA | GTG | ACG | GAT | 1318 |
|---|---|---|---|---|---|---|---|---|---|---|---|---|---|---|---|---|
| His | Ala | Gly | Leu | Ser | Asp | Asp | Asp | Ile | Phe | Ala | Gly | Lys | Val | Thr | Asp | |
| | 305 | | | | | 310 | | | | | 315 | | | | | |

-continued

| | | | | | | | | | | | | | | | | |
|---|---|---|---|---|---|---|---|---|---|---|---|---|---|---|---|---|
| AAA | TGG | AGA | AGC | TTT | ATG | AAG | AAG | CAA | ATC | CAG | AGG | GCA | AGA | AAG | TTC | 1366 |
| Lys | Trp | Arg | Ser | Phe | Met | Lys | Lys | Gln | Ile | Gln | Arg | Ala | Arg | Lys | Phe | |
| 320 | | | | | 325 | | | | | 330 | | | | | 335 | |
| TTT | GAT | GAG | GCA | GAG | GAA | GGA | GTG | ACA | CAA | CTG | AGC | TCA | GCT | AGT | AGA | 1414 |
| Phe | Asp | Glu | Ala | Glu | Glu | Gly | Val | Thr | Gln | Leu | Ser | Ser | Ala | Ser | Arg | |
| | | | | 340 | | | | | 345 | | | | | 350 | | |
| TGG | CCT | GTA | TGG | GCT | TCT | TTG | CTG | TTG | TAC | CGC | CAG | ATA | CTC | GAC | GAG | 1462 |
| Trp | Pro | Val | Trp | Ala | Ser | Leu | Leu | Leu | Tyr | Arg | Gln | Ile | Leu | Asp | Glu | |
| | | | 355 | | | | | 360 | | | | | 365 | | | |
| ATC | GAA | GCC | AAT | GAC | TAC | AAC | AAC | TTC | ACA | AAG | AGA | GCT | TAT | GTG | AGC | 1510 |
| Ile | Glu | Ala | Asn | Asp | Tyr | Asn | Asn | Phe | Thr | Lys | Arg | Ala | Tyr | Val | Ser | |
| | | 370 | | | | | 375 | | | | | 380 | | | | |
| AAA | TCA | AAG | AAG | CTA | ATT | TCC | TTA | CCT | ATT | GCT | AAT | GCA | AAA | TCT | CTT | 1558 |
| Lys | Ser | Lys | Lys | Leu | Ile | Ser | Leu | Pro | Ile | Ala | Asn | Ala | Lys | Ser | Leu | |
| | 385 | | | | | 390 | | | | | 395 | | | | | |
| GTG | CCC | CCA | ACA | AGA | ACT | CTT | GTC | TCC | TCT | AGC | TAAGGCATAG | | | ACATCAGATT | | 1611 |
| Val | Pro | Pro | Thr | Arg | Thr | Leu | Val | Ser | Ser | Ser | | | | | | |
| 400 | | | | | 405 | | | | | 410 | | | | | | |

| | | | | | |
|---|---|---|---|---|---|
| TAAATTAAAG | CAAGAAAGCA | TATCCTGTTA | AAAAAGAAAG | AATTTATAAA | GTAGATATTG | 1671 |
| GTGTATTGAT | GTCACTTGTA | TATCATCAAA | AGTAGGTAGT | AAAATTCAAT | ATAACAATCT | 1731 |
| TTAGTGGTTG | TATGTATCTT | AACAATCTTA | AACCCTTCGA | GGGAAATTCT | TTTTGGTTCA | 1791 |
| TTGG | | | | | | 1795 |

( 2 ) INFORMATION FOR SEQ ID NO:2:

( i ) SEQUENCE CHARACTERISTICS:
      ( A ) LENGTH: 410 amino acids
      ( B ) TYPE: amino acid
      ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Ser | Val | Ala | Leu | Leu | Trp | Val | Val | Ser | Pro | Cys | Glu | Val | Ser | Asn |
| 1 | | | | 5 | | | | | 10 | | | | | 15 | |
| Gly | Thr | Gly | Phe | Leu | Asp | Ser | Ile | Arg | Glu | Gly | Asn | Arg | Val | Phe | Asp |
| | | | 20 | | | | | 25 | | | | | 30 | | |
| Leu | Ser | Arg | Tyr | Arg | Asn | Leu | Val | Cys | Asn | Glu | Arg | Asn | Lys | Arg | Gly |
| | | 35 | | | | | 40 | | | | | 45 | | | |
| Gly | Lys | Gln | Arg | Trp | Asn | Phe | Gly | Ser | Val | Arg | Ser | Ala | Met | Val | Ala |
| | 50 | | | | | 55 | | | | | 60 | | | | |
| Thr | Pro | Ala | Gly | Glu | Met | Ala | Thr | Met | Thr | Ser | Glu | Gln | Met | Val | Tyr |
| 65 | | | | | 70 | | | | | 75 | | | | | 80 |
| Asp | Val | Val | Leu | Lys | Gln | Ala | Ala | Leu | Val | Lys | Arg | Gln | Leu | Arg | Ser |
| | | | | 85 | | | | | 90 | | | | | 95 | |
| Thr | Asp | Asp | Leu | Glu | Val | Lys | Pro | Glu | Ile | Pro | Leu | Gln | Ala | Asn | Leu |
| | | | 100 | | | | | 105 | | | | | 110 | | |
| Ser | Leu | Leu | Ser | Glu | Ala | Tyr | Asp | Arg | Cys | Ser | Glu | Val | Cys | Ala | Glu |
| | | | 115 | | | | | 120 | | | | | 125 | | |
| Tyr | Ala | Lys | Thr | Phe | Tyr | Leu | Gly | Thr | Met | Leu | Met | Thr | Pro | Glu | Arg |
| | | 130 | | | | | 135 | | | | | 140 | | | |
| Arg | Arg | Ala | Ile | Trp | Ala | Ile | Tyr | Val | Trp | Cys | Arg | Arg | Thr | Asp | Glu |
| 145 | | | | | 150 | | | | | 155 | | | | | 160 |
| Leu | Val | Asp | Gly | Pro | Asn | Ala | Ser | His | Ile | Thr | Pro | Gln | Gly | Leu | Asp |
| | | | | 165 | | | | | 170 | | | | | 175 | |
| Arg | Trp | Glu | Asp | Leu | Leu | Glu | Asp | Val | Phe | Ser | Gly | Arg | Pro | Phe | Asp |
| | | | 180 | | | | | 185 | | | | | 190 | | |

```
Met  Leu  Asp  Ala  Ala  Leu  Ser  Asp  Thr  Val  Ser  Lys  Phe  Pro  Val  Asp
          195                      200                      205

Ile  Gln  Pro  Phe  Arg  Asp  Met  Ile  Glu  Gly  Met  Arg  Met  Asp  Leu  Arg
     210                      215                      220

Lys  Ser  Arg  Tyr  Arg  Asn  Phe  Asp  Glu  Leu  Tyr  Leu  Tyr  Cys  Tyr  Tyr
225                      230                      235                      240

Val  Ala  Gly  Thr  Val  Gly  Leu  Met  Ser  Val  Pro  Ile  Met  Gly  Ile  Ala
               245                      250                      255

Pro  Asp  Ser  Lys  Ala  Thr  Thr  Glu  Asn  Val  Tyr  Asn  Ala  Ala  Leu  Ala
               260                      265                      270

Leu  Gly  Ile  Ala  Asn  Gln  Leu  Thr  Asn  Ile  Leu  Arg  Asp  Val  Gly  Glu
          275                      280                      285

Asp  Ala  Arg  Arg  Gly  Arg  Val  Tyr  Leu  Pro  Gln  Asp  Glu  Leu  Ala  His
     290                      295                      300

Ala  Gly  Leu  Ser  Asp  Asp  Asp  Ile  Phe  Ala  Gly  Lys  Val  Thr  Asp  Lys
305                      310                      315                      320

Trp  Arg  Ser  Phe  Met  Lys  Lys  Gln  Ile  Gln  Arg  Ala  Arg  Lys  Phe  Phe
               325                      330                      335

Asp  Glu  Ala  Glu  Glu  Gly  Val  Thr  Gln  Leu  Ser  Ser  Ala  Ser  Arg  Trp
               340                      345                      350

Pro  Val  Trp  Ala  Ser  Leu  Leu  Leu  Tyr  Arg  Gln  Ile  Leu  Asp  Glu  Ile
          355                      360                      365

Glu  Ala  Asn  Asp  Tyr  Asn  Asn  Phe  Thr  Lys  Arg  Ala  Tyr  Val  Ser  Lys
     370                      375                      380

Ser  Lys  Lys  Leu  Ile  Ser  Leu  Pro  Ile  Ala  Asn  Ala  Lys  Ser  Leu  Val
385                      390                      395                      400

Pro  Pro  Thr  Arg  Thr  Leu  Val  Ser  Ser  Ser
               405                      410
```

(2) INFORMATION FOR SEQ ID NO:3:

(i) SEQUENCE CHARACTERISTICS:
        (A) LENGTH: 1316 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1239

(xi) SEQUENCE DESCRIPTION: SEQ ID NO:3:

```
ATG  TCT  GTT  GCC  TTG  TTA  TGG  GTT  GTT  TCA  CCT  TGT  GAG  GTC  TCA  AAT     48
Met  Ser  Val  Ala  Leu  Leu  Trp  Val  Val  Ser  Pro  Cys  Glu  Val  Ser  Asn
               415                      420                      425

GGG  ACA  GGA  TTC  TTG  GAT  TCA  ATC  CGG  GAG  GGA  AAC  CGG  GTT  TTT  GAT     96
Gly  Thr  Gly  Phe  Leu  Asp  Ser  Ile  Arg  Glu  Gly  Asn  Arg  Val  Phe  Asp
               430                      435                      440

TGG  TCG  AGG  CAT  AGG  AAT  TTA  GTG  TGC  AAT  GAG  AGA  AAC  AAG  AGA  GGT    144
Trp  Ser  Arg  His  Arg  Asn  Leu  Val  Cys  Asn  Glu  Arg  Asn  Lys  Arg  Gly
               445                      450                      455

GTG  GAA  CAA  ATG  TGG  AAT  TTT  GGT  TCT  GTA  AAG  TCT  GCT  ATG  GTG  GCT    192
Val  Glu  Gln  Met  Trp  Asn  Phe  Gly  Ser  Val  Lys  Ser  Ala  Met  Val  Ala
     460                      465                      470

ACA  CCG  GCG  GGA  GAA  ATG  GCG  ACG  ATG  ACA  TCA  GAA  CAG  ATG  GTT  TAT    240
Thr  Pro  Ala  Gly  Glu  Met  Ala  Thr  Met  Thr  Ser  Glu  Gln  Met  Val  Tyr
475                      480                      485                      490
```

| | | | | | | | | | | | | | | | | |
|---|---|---|---|---|---|---|---|---|---|---|---|---|---|---|---|---|
| GAT | GTG | GTA | TTG | AAA | CAA | ACA | GCT | TTA | GTG | AAG | AGG | CAG | TTG | AGA | TCT | 288 |
| Asp | Val | Val | Leu | Lys | Gln | Thr | Ala | Leu | Val | Lys | Arg | Gln | Leu | Arg | Ser | |
| | | | | 495 | | | | | 500 | | | | | 505 | | |
| ACT | GAT | GAT | TTA | GAA | GTG | AAG | GCG | GAG | ATC | CCT | CTC | CCG | GGG | AAT | TTG | 336 |
| Thr | Asp | Asp | Leu | Glu | Val | Lys | Ala | Glu | Ile | Pro | Leu | Pro | Gly | Asn | Leu | |
| | | | | 510 | | | | | 515 | | | | | 520 | | |
| AGC | TTG | TTG | AGT | GAA | GCA | TAT | GAT | AGG | TGT | AGC | GAA | GTA | TGT | GCA | GAG | 384 |
| Ser | Leu | Leu | Ser | Glu | Ala | Tyr | Asp | Arg | Cys | Ser | Glu | Val | Cys | Ala | Glu | |
| | | | | 525 | | | | | 530 | | | | | 535 | | |
| TAT | GCG | AAG | ACA | TTT | TAC | TTA | GGA | ACT | ATG | CTA | ATG | ACT | CCA | GAG | AGA | 432 |
| Tyr | Ala | Lys | Thr | Phe | Tyr | Leu | Gly | Thr | Met | Leu | Met | Thr | Pro | Glu | Arg | |
| | | | | 540 | | | | | 545 | | | | | 550 | | |
| AGA | AGG | GCT | ATT | TGG | GCA | ATA | TAT | GTA | TGG | TGC | AGG | AGA | ACA | GAC | GAA | 480 |
| Arg | Arg | Ala | Ile | Trp | Ala | Ile | Tyr | Val | Trp | Cys | Arg | Arg | Thr | Asp | Glu | |
| 555 | | | | | 560 | | | | | 565 | | | | | 570 | |
| CTT | GTT | GAT | GGC | CCG | AAT | GCA | TCA | CAT | ATT | ACT | CCA | CAA | GCC | TTA | GAT | 528 |
| Leu | Val | Asp | Gly | Pro | Asn | Ala | Ser | His | Ile | Thr | Pro | Gln | Ala | Leu | Asp | |
| | | | | 575 | | | | | 580 | | | | | 585 | | |
| AGG | TGG | GAA | GAC | CGG | CTG | GAA | GAT | GTT | TTC | AGT | GGG | CGG | CCA | TTT | GAC | 576 |
| Arg | Trp | Glu | Asp | Arg | Leu | Glu | Asp | Val | Phe | Ser | Gly | Arg | Pro | Phe | Asp | |
| | | | | 590 | | | | | 595 | | | | | 600 | | |
| ATG | CTC | GAT | GCT | GCT | TTG | TCC | GAT | ACT | GTT | TCC | AAG | TTT | CCA | GTT | GAT | 624 |
| Met | Leu | Asp | Ala | Ala | Leu | Ser | Asp | Thr | Val | Ser | Lys | Phe | Pro | Val | Asp | |
| | | | | 605 | | | | | 610 | | | | | 615 | | |
| ATT | CAG | CCG | TTC | AGA | GAT | ATG | ATC | GAA | GGA | ATG | CGT | ATG | GAC | TTG | AGG | 672 |
| Ile | Gln | Pro | Phe | Arg | Asp | Met | Ile | Glu | Gly | Met | Arg | Met | Asp | Leu | Arg | |
| | | | | 620 | | | | | 625 | | | | | 630 | | |
| AAG | TCG | AGA | TAC | AGA | AAC | TTT | GAT | GAG | CTA | TAC | CTA | TAT | TGT | TAT | TAC | 720 |
| Lys | Ser | Arg | Tyr | Arg | Asn | Phe | Asp | Glu | Leu | Tyr | Leu | Tyr | Cys | Tyr | Tyr | |
| 635 | | | | | 640 | | | | | 645 | | | | | 650 | |
| GTT | GCT | GGT | ACA | GTT | GGG | TTG | ATG | AGT | GTT | CCA | ATT | ATG | GGC | ATC | GCA | 768 |
| Val | Ala | Gly | Thr | Val | Gly | Leu | Met | Ser | Val | Pro | Ile | Met | Gly | Ile | Ala | |
| | | | | 655 | | | | | 660 | | | | | 665 | | |
| CCT | GAA | TCA | AAG | GCA | ACA | ACA | GAG | AGT | GTA | TAT | AAT | GCA | GCT | TTG | GCT | 816 |
| Pro | Glu | Ser | Lys | Ala | Thr | Thr | Glu | Ser | Val | Tyr | Asn | Ala | Ala | Leu | Ala | |
| | | | | 670 | | | | | 675 | | | | | 680 | | |
| TTG | GGT | ATC | GCG | AAT | CAA | CTA | ACC | AAC | ATT | CTC | AGA | GAT | GTC | GGA | GAA | 864 |
| Leu | Gly | Ile | Ala | Asn | Gln | Leu | Thr | Asn | Ile | Leu | Arg | Asp | Val | Gly | Glu | |
| | | | | 685 | | | | | 690 | | | | | 695 | | |
| GAT | GCC | AGA | AGA | GGA | AGA | GTC | TAC | TTA | CCT | CAA | GAT | GAA | TTA | GCA | CAG | 912 |
| Asp | Ala | Arg | Arg | Gly | Arg | Val | Tyr | Leu | Pro | Gln | Asp | Glu | Leu | Ala | Gln | |
| | | | | 700 | | | | | 705 | | | | | 710 | | |
| GCA | GGT | CTC | TCC | GAC | GAT | GAC | ATA | TTT | ACT | GGA | AAA | GTG | ACT | GAT | AAA | 960 |
| Ala | Gly | Leu | Ser | Asp | Asp | Asp | Ile | Phe | Thr | Gly | Lys | Val | Thr | Asp | Lys | |
| | | | | 715 | | | | | 720 | | | | | 725 | | 730 |
| TGG | AGA | AGC | TTT | ATG | AAG | AAG | CAA | TTC | CAG | AGG | GCA | AGA | AAG | TTC | TTC | 1008 |
| Trp | Arg | Ser | Phe | Met | Lys | Lys | Gln | Phe | Gln | Arg | Ala | Arg | Lys | Phe | Phe | |
| | | | | 735 | | | | | 740 | | | | | 745 | | |
| AAT | GAG | GCA | GAG | GAA | GGA | GTT | ACA | CAA | CTG | AGC | TCA | GCT | AGC | AGA | TGG | 1056 |
| Asn | Glu | Ala | Glu | Glu | Gly | Val | Thr | Gln | Leu | Ser | Ser | Ala | Ser | Arg | Trp | |
| | | | | 750 | | | | | 755 | | | | | 760 | | |
| CCT | GTA | TGG | GCA | TCT | TTG | CTG | TTG | TAC | CGC | CAA | ATA | CTC | GAC | GAG | ATC | 1104 |
| Pro | Val | Trp | Ala | Ser | Leu | Leu | Leu | Tyr | Arg | Gln | Ile | Leu | Asp | Glu | Ile | |
| | | | | 765 | | | | | 770 | | | | | 775 | | |
| GAA | GCC | AAT | GAC | TAC | AAC | AAC | TTC | ACA | AAG | AGA | GCT | TAT | GTG | AGC | AAA | 1152 |
| Glu | Ala | Asn | Asp | Tyr | Asn | Asn | Phe | Thr | Lys | Arg | Ala | Tyr | Val | Ser | Lys | |
| | | | | 780 | | | | | 785 | | | | | 790 | | |
| TCA | AAG | AAG | CTA | ATT | TCC | TTA | CCT | ATT | GCT | TAT | GCA | AAA | TCT | CTT | GTG | 1200 |
| Ser | Lys | Lys | Leu | Ile | Ser | Leu | Pro | Ile | Ala | Tyr | Ala | Lys | Ser | Leu | Val | |
| | | | | 795 | | | | | 800 | | | | | 805 | | 810 |

```
CCC  CCT  ACA  AGA  ACT  CTT  GTC  ACC  TCT  ATA  GCT  AAG  GCA  TAGACATCAG              1249
Pro  Pro  Thr  Arg  Thr  Leu  Val  Thr  Ser  Ile  Ala  Lys  Ala
               815                           820

ATTTAAATTA  AAGCAAGAAA  GCATATACTG  TTAAAAAGA  AAGAATTTAT  AAAGTAGATA                    1309

TTGGTGT                                                                                  1316
```

(2) INFORMATION FOR SEQ ID NO:4:

(i) SEQUENCE CHARACTERISTICS:
  (A) LENGTH: 413 amino acids
  (B) TYPE: amino acid
  (D) TOPOLOGY: linear (ii) MOLECULE TYPE: protein (xi) SEQUENCE DESCRIPTION: SEQ ID NO:4:

```
Met  Ser  Val  Ala  Leu  Leu  Trp  Val  Val  Ser  Pro  Cys  Glu  Val  Ser  Asn
 1              5                        10                            15

Gly  Thr  Gly  Phe  Leu  Asp  Ser  Ile  Arg  Glu  Gly  Asn  Arg  Val  Phe  Asp
               20                        25                       30

Trp  Ser  Arg  His  Arg  Asn  Leu  Val  Cys  Asn  Glu  Arg  Asn  Lys  Arg  Gly
          35                        40                       45

Val  Glu  Gln  Met  Trp  Asn  Phe  Gly  Ser  Val  Lys  Ser  Ala  Met  Val  Ala
     50                        55                       60

Thr  Pro  Ala  Gly  Glu  Met  Ala  Thr  Met  Thr  Ser  Gln  Met  Val  Tyr
 65                       70                       75                       80

Asp  Val  Val  Leu  Lys  Gln  Thr  Ala  Leu  Val  Lys  Arg  Gln  Leu  Arg  Ser
               85                        90                       95

Thr  Asp  Asp  Leu  Glu  Val  Lys  Ala  Glu  Ile  Pro  Leu  Pro  Gly  Asn  Leu
              100                       105                      110

Ser  Leu  Leu  Ser  Glu  Ala  Tyr  Asp  Arg  Cys  Ser  Glu  Val  Cys  Ala  Glu
              115                       120                      125

Tyr  Ala  Lys  Thr  Phe  Tyr  Leu  Gly  Thr  Met  Leu  Met  Thr  Pro  Glu  Arg
     130                       135                      140

Arg  Arg  Ala  Ile  Trp  Ala  Ile  Tyr  Val  Trp  Cys  Arg  Arg  Thr  Asp  Glu
145                      150                       155                     160

Leu  Val  Asp  Gly  Pro  Asn  Ala  Ser  His  Ile  Thr  Pro  Gln  Ala  Leu  Asp
               165                       170                      175

Arg  Trp  Glu  Asp  Arg  Leu  Glu  Asp  Val  Phe  Ser  Gly  Arg  Pro  Phe  Asp
               180                       185                      190

Met  Leu  Asp  Ala  Ala  Leu  Ser  Asp  Thr  Val  Ser  Lys  Phe  Pro  Val  Asp
          195                       200                      205

Ile  Gln  Pro  Phe  Arg  Asp  Met  Ile  Glu  Gly  Met  Arg  Met  Asp  Leu  Arg
     210                       215                      220

Lys  Ser  Arg  Tyr  Arg  Asn  Phe  Asp  Glu  Leu  Tyr  Leu  Tyr  Cys  Tyr  Tyr
225                      230                       235                     240

Val  Ala  Gly  Thr  Val  Gly  Leu  Met  Ser  Val  Pro  Ile  Met  Gly  Ile  Ala
               245                       250                      255

Pro  Glu  Ser  Lys  Ala  Thr  Thr  Glu  Ser  Val  Tyr  Asn  Ala  Ala  Leu  Ala
               260                       265                      270

Leu  Gly  Ile  Ala  Asn  Gln  Leu  Thr  Asn  Ile  Leu  Arg  Asp  Val  Gly  Glu
          275                       280                      285

Asp  Ala  Arg  Arg  Gly  Arg  Val  Tyr  Leu  Pro  Gln  Asp  Glu  Leu  Ala  Gln
     290                       295                      300

Ala  Gly  Leu  Ser  Asp  Asp  Asp  Ile  Phe  Thr  Gly  Lys  Val  Thr  Asp  Lys
305                       310                      315                     320
```

```
Trp Arg Ser Phe Met Lys Lys Gln Phe Gln Arg Ala Arg Lys Phe Phe
            325                 330                 335

Asn Glu Ala Glu Glu Gly Val Thr Gln Leu Ser Ser Ala Ser Arg Trp
            340                 345                 350

Pro Val Trp Ala Ser Leu Leu Leu Tyr Arg Gln Ile Leu Asp Glu Ile
            355                 360                 365

Glu Ala Asn Asp Tyr Asn Asn Phe Thr Lys Arg Ala Tyr Val Ser Lys
            370                 375                 380

Ser Lys Lys Leu Ile Ser Leu Pro Ile Ala Tyr Ala Lys Ser Leu Val
385                 390                 395                 400

Pro Pro Thr Arg Thr Leu Val Thr Ser Ile Ala Lys Ala
                405                 410
```

( 2 ) INFORMATION FOR SEQ ID NO:5:

( i ) SEQUENCE CHARACTERISTICS:
( A ) LENGTH: 1826 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 367..1596

( x i ) SEQUENCE DESCRIPTION: SEQ ID NO:5:

```
AGAAGAAAAA CAAAGAAACT CCTTCGATTC TTGAAGAGTA CACAGCAGCA AACAAGAAAA        60

TTAAAGTGGC TATTTTTGAA AAGCCATTGT TACAAGAAAA TTAAGAAGCA AGAAACAGG        120

TTATTTCTG CTTGAGTTAG GAAAAGCTGA GTTGCTTTCT TTGTGGTCTT TTTATAATCT        180

TTTACATAAC AGGAAGTAGG TATTTTCTTG AAAGTTGATT TAGACTCTAG TGGGAATCTA        240

CTAGGAGTAT TTTTTTTATT TTTTATTTTT TATAAATTAA GCAGAGGAGG GAAGGAAACA        300

GAAAACAGAA AGTAAGACAA AAAAACCTTG GAATTGTTTT AGACAACCAA GGTTTTGTTG        360

TTCAGA ATG TCT GTT GCC TTG TTA TGG GTT GTT TCA CCT TGT GAG GTC          408
       Met Ser Val Ala Leu Leu Trp Val Val Ser Pro Cys Glu Val
           415                 420                 425

TCA AAT GGG ACA GGA TTC TTG GAT TCA GTA AGG GAG GGA AAC CGG GTT          456
Ser Asn Gly Thr Gly Phe Leu Asp Ser Val Arg Glu Gly Asn Arg Val
        430                 435                 440

TTT GAC TCG TCG AGG CAT AGG AAT TTA GTG TGC AAT GAG AGA ATC AAA          504
Phe Asp Ser Ser Arg His Arg Asn Leu Val Cys Asn Glu Arg Ile Lys
    445                 450                 455

AGA GGT GTG AAA CAA AGG TGG AAT TTT GGT TCT GTA CGG TCT GCG ATG          552
Arg Gly Val Lys Gln Arg Trp Asn Phe Gly Ser Val Arg Ser Ala Met
460                 465                 470                 475

GTG GCT ACA CCA ACG GGA GAA ATG GCG ACA ATG ACA TCA GAA CAG AAG          600
Val Ala Thr Pro Thr Gly Glu Met Ala Thr Met Thr Ser Glu Gln Lys
                480                 485                 490

GTT TAT GAT GTG GTA TTG AAA CAA GCA GCT TTA GTG AAA AGG CAG CTG          648
Val Tyr Asp Val Val Leu Lys Gln Ala Ala Leu Val Lys Arg Gln Leu
            495                 500                 505

AGA TCT ACT GAT GAT TTA GAA GTG AAG CCG GAG ATC CCT CTC CCC GGG          696
Arg Ser Thr Asp Asp Leu Glu Val Lys Pro Glu Ile Pro Leu Pro Gly
        510                 515                 520

AAT TTG AGC TTG TTA AGT GAA GCA TAT GAT AGG TGT AGT GAA GTA TGC          744
Asn Leu Ser Leu Leu Ser Glu Ala Tyr Asp Arg Cys Ser Glu Val Cys
    525                 530                 535

GCA GAG TAT GCA AAG ACA TTT TAC TTA GGA ACT ATG CTA ATG ACT CCA          792
```

| Ala | Glu | Tyr | Ala | Lys | Thr | Phe | Tyr | Leu | Gly | Thr | Met | Leu | Met | Thr | Pro | |
|-----|-----|-----|-----|-----|-----|-----|-----|-----|-----|-----|-----|-----|-----|-----|-----|---|
| 540 |     |     |     | 545 |     |     |     |     | 550 |     |     |     |     |     | 555 |   |

| GAG | AGA | AGA | AGG | GCT | ATT | TGG | GCA | ATA | TAT | GTA | TGG | TGC | AGG | AGA | ACA | 840 |
|-----|-----|-----|-----|-----|-----|-----|-----|-----|-----|-----|-----|-----|-----|-----|-----|-----|
| Glu | Arg | Arg | Arg | Ala | Ile | Trp | Ala | Ile | Tyr | Val | Trp | Cys | Arg | Arg | Thr | |
|     |     |     |     | 560 |     |     |     |     | 565 |     |     |     |     | 570 |     | |

| GAT | GAA | CTT | GTT | GAT | GGC | CCG | AAT | GCA | TCA | CAT | ATT | ACT | CCA | CAA | GCC | 888 |
|-----|-----|-----|-----|-----|-----|-----|-----|-----|-----|-----|-----|-----|-----|-----|-----|-----|
| Asp | Glu | Leu | Val | Asp | Gly | Pro | Asn | Ala | Ser | His | Ile | Thr | Pro | Gln | Ala | |
|     |     |     | 575 |     |     |     |     | 580 |     |     |     |     | 585 |     |     | |

| TTA | GAT | AGG | TGG | GAA | GAC | CGG | CTG | GAA | GAT | GTT | TTC | AGT | GGG | CGG | CCA | 936 |
|-----|-----|-----|-----|-----|-----|-----|-----|-----|-----|-----|-----|-----|-----|-----|-----|-----|
| Leu | Asp | Arg | Trp | Glu | Asp | Arg | Leu | Glu | Asp | Val | Phe | Ser | Gly | Arg | Pro | |
|     |     | 590 |     |     |     |     | 595 |     |     |     |     | 600 |     |     |     | |

| TTT | GAT | ATG | CTC | GAT | GCT | GCT | TTG | TCC | GAT | ACT | GTT | TCC | CAG | TTT | CCA | 984 |
|-----|-----|-----|-----|-----|-----|-----|-----|-----|-----|-----|-----|-----|-----|-----|-----|-----|
| Phe | Asp | Met | Leu | Asp | Ala | Ala | Leu | Ser | Asp | Thr | Val | Ser | Gln | Phe | Pro | |
|     | 605 |     |     |     | 610 |     |     |     |     | 615 |     |     |     |     |     | |

| GTT | GAT | ATT | CAG | CCG | TTC | AGA | GAT | ATG | ATT | GAA | GGA | ATG | CGT | ATG | GAC | 1032 |
|-----|-----|-----|-----|-----|-----|-----|-----|-----|-----|-----|-----|-----|-----|-----|-----|------|
| Val | Asp | Ile | Gln | Pro | Phe | Arg | Asp | Met | Ile | Glu | Gly | Met | Arg | Met | Asp | |
| 620 |     |     |     |     | 625 |     |     |     |     | 630 |     |     |     |     | 635 | |

| TTG | AGG | AAG | TCA | AGA | TAC | AGA | AAC | TTT | GAT | GAG | CTA | TAC | CTA | TAT | TGT | 1080 |
|-----|-----|-----|-----|-----|-----|-----|-----|-----|-----|-----|-----|-----|-----|-----|-----|------|
| Leu | Arg | Lys | Ser | Arg | Tyr | Arg | Asn | Phe | Asp | Glu | Leu | Tyr | Leu | Tyr | Cys | |
|     |     |     |     | 640 |     |     |     |     | 645 |     |     |     |     | 650 |     | |

| TAT | TAC | GTT | GCT | GGT | ACG | GTT | GGG | TTG | ATG | AGT | GTT | CCA | ATT | ATG | GGT | 1128 |
|-----|-----|-----|-----|-----|-----|-----|-----|-----|-----|-----|-----|-----|-----|-----|-----|------|
| Tyr | Tyr | Val | Ala | Gly | Thr | Val | Gly | Leu | Met | Ser | Val | Pro | Ile | Met | Gly | |
|     |     |     | 655 |     |     |     |     | 660 |     |     |     |     | 665 |     |     | |

| ATT | GCA | CCT | GAT | TCA | AAG | GCA | ACA | ACA | GAG | AGT | GTA | TAT | AAT | GCA | GCT | 1176 |
|-----|-----|-----|-----|-----|-----|-----|-----|-----|-----|-----|-----|-----|-----|-----|-----|------|
| Ile | Ala | Pro | Asp | Ser | Lys | Ala | Thr | Thr | Glu | Ser | Val | Tyr | Asn | Ala | Ala | |
|     |     | 670 |     |     |     |     | 675 |     |     |     |     | 680 |     |     |     | |

| TTG | GCT | TTA | GGG | ATC | GCA | AAT | CAA | CTA | ACC | AAC | ATA | CTC | AGA | GAT | GTC | 1224 |
|-----|-----|-----|-----|-----|-----|-----|-----|-----|-----|-----|-----|-----|-----|-----|-----|------|
| Leu | Ala | Leu | Gly | Ile | Ala | Asn | Gln | Leu | Thr | Asn | Ile | Leu | Arg | Asp | Val | |
|     | 685 |     |     |     |     | 690 |     |     |     |     | 695 |     |     |     |     | |

| GGA | GAA | GAT | GCC | AGA | AGA | GGA | AGA | GTC | TAC | TTA | CCT | CAA | GAT | GAG | TTA | 1272 |
|-----|-----|-----|-----|-----|-----|-----|-----|-----|-----|-----|-----|-----|-----|-----|-----|------|
| Gly | Glu | Asp | Ala | Arg | Arg | Gly | Arg | Val | Tyr | Leu | Pro | Gln | Asp | Glu | Leu | |
| 700 |     |     |     |     | 705 |     |     |     |     | 710 |     |     |     |     | 715 | |

| GCA | CAG | GCA | GGT | CTC | TCC | GAC | AAT | GAC | ATT | TTT | GCT | GGA | AAA | GTG | ACT | 1320 |
|-----|-----|-----|-----|-----|-----|-----|-----|-----|-----|-----|-----|-----|-----|-----|-----|------|
| Ala | Gln | Ala | Gly | Leu | Ser | Asp | Asn | Asp | Ile | Phe | Ala | Gly | Lys | Val | Thr | |
|     |     |     |     | 720 |     |     |     |     | 725 |     |     |     |     | 730 |     | |

| GAT | AAA | TGG | AGA | AGC | TTT | ATG | AAG | AAG | CAA | ATC | CAG | AGG | GCA | AGA | AAA | 1368 |
|-----|-----|-----|-----|-----|-----|-----|-----|-----|-----|-----|-----|-----|-----|-----|-----|------|
| Asp | Lys | Trp | Arg | Ser | Phe | Met | Lys | Lys | Gln | Ile | Gln | Arg | Ala | Arg | Lys | |
|     |     |     | 735 |     |     |     |     | 740 |     |     |     |     | 745 |     |     | |

| TTC | TTC | GAC | GAG | GCA | GAG | GAA | GGA | GTG | ACA | CAA | CTG | AGC | TCA | GCT | AGT | 1416 |
|-----|-----|-----|-----|-----|-----|-----|-----|-----|-----|-----|-----|-----|-----|-----|-----|------|
| Phe | Phe | Asp | Glu | Ala | Glu | Glu | Gly | Val | Thr | Gln | Leu | Ser | Ser | Ala | Ser | |
|     |     |     | 750 |     |     |     |     | 755 |     |     |     |     | 760 |     |     | |

| AGA | TGG | CCT | GTA | TGG | GCA | TCT | TTG | CTG | TTG | TAC | CGC | CAG | ATA | CTC | GAC | 1464 |
|-----|-----|-----|-----|-----|-----|-----|-----|-----|-----|-----|-----|-----|-----|-----|-----|------|
| Arg | Trp | Pro | Val | Trp | Ala | Ser | Leu | Leu | Leu | Tyr | Arg | Gln | Ile | Leu | Asp | |
|     | 765 |     |     |     |     | 770 |     |     |     |     | 775 |     |     |     |     | |

| GAG | ATT | GAA | GCC | AAT | GAC | TAC | AAC | AAC | TTC | ACA | AGG | AGA | GCT | TAT | GTG | 1512 |
|-----|-----|-----|-----|-----|-----|-----|-----|-----|-----|-----|-----|-----|-----|-----|-----|------|
| Glu | Ile | Glu | Ala | Asn | Asp | Tyr | Asn | Asn | Phe | Thr | Arg | Arg | Ala | Tyr | Val | |
| 780 |     |     |     |     | 785 |     |     |     |     | 790 |     |     |     |     | 795 | |

| AGC | AAA | CCA | AAG | AAG | CTA | ATT | TCC | TTA | CCT | ATT | GCT | TAT | GCA | AAA | TCT | 1560 |
|-----|-----|-----|-----|-----|-----|-----|-----|-----|-----|-----|-----|-----|-----|-----|-----|------|
| Ser | Lys | Pro | Lys | Lys | Leu | Ile | Ser | Leu | Pro | Ile | Ala | Tyr | Ala | Lys | Ser | |
|     |     |     |     | 800 |     |     |     |     | 805 |     |     |     |     | 810 |     | |

| CTT | GTG | CCC | CCT | ACA | AGA | ACT | CTT | GTC | ACC | TCT | AGC | TAAGGCATAG | 1606 |
|-----|-----|-----|-----|-----|-----|-----|-----|-----|-----|-----|-----|-----|-----|
| Leu | Val | Pro | Pro | Thr | Arg | Thr | Leu | Val | Thr | Ser | Ser | | |
|     |     |     | 815 |     |     |     |     | 820 |     |     |     | | |

| ACATCAGAAT | TAAATTAAAG | CAAGAAAGCA | TATATTATTA | TTATTATACT | GTTAAAAGGA | 1666 |
| AAGAATTTGT | AAAGTAGATA | TTGTTGTATT | GATGTCACTG | GTATATCATC | AAAAGTAGGT | 1726 |
| AGTAAAATCC | AATATAACAA | TTTATAGTAG | TTGTATCTTC | ACAATCTTAA | ACCCTTTGAG | 1786 |
| GGACATTCTT | TTTGGTTCAT | TGGAAAAAAT | TGTTGACTCC | | | 1826 |

( 2 ) INFORMATION FOR SEQ ID NO:6:

( i ) SEQUENCE CHARACTERISTICS:
        ( A ) LENGTH: 410 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Ser Val Ala Leu Leu Trp Val Val Ser Pro Cys Glu Val Ser Asn
  1               5                  10                 15
Gly Thr Gly Phe Leu Asp Ser Val Arg Glu Gly Asn Arg Val Phe Asp
                 20                 25                 30
Ser Ser Arg His Arg Asn Leu Val Cys Asn Glu Arg Ile Lys Arg Gly
             35                 40                 45
Val Lys Gln Arg Trp Asn Phe Gly Ser Val Arg Ser Ala Met Val Ala
         50                 55                 60
Thr Pro Thr Gly Glu Met Ala Thr Met Thr Ser Glu Gln Lys Val Tyr
 65                 70                 75                 80
Asp Val Val Leu Lys Gln Ala Ala Leu Val Lys Arg Gln Leu Arg Ser
                 85                 90                 95
Thr Asp Asp Leu Glu Val Lys Pro Glu Ile Pro Leu Pro Gly Asn Leu
            100                105                110
Ser Leu Leu Ser Glu Ala Tyr Asp Arg Cys Ser Glu Val Cys Ala Glu
            115                120                125
Tyr Ala Lys Thr Phe Tyr Leu Gly Thr Met Leu Met Thr Pro Glu Arg
        130                135                140
Arg Arg Ala Ile Trp Ala Ile Tyr Val Trp Cys Arg Arg Thr Asp Glu
145                150                155                160
Leu Val Asp Gly Pro Asn Ala Ser His Ile Thr Pro Gln Ala Leu Asp
                165                170                175
Arg Trp Glu Asp Arg Leu Glu Asp Val Phe Ser Gly Arg Pro Phe Asp
            180                185                190
Met Leu Asp Ala Ala Leu Ser Asp Thr Val Ser Gln Phe Pro Val Asp
            195                200                205
Ile Gln Pro Phe Arg Asp Met Ile Glu Gly Met Arg Met Asp Leu Arg
210                215                220
Lys Ser Arg Tyr Arg Asn Phe Asp Glu Leu Tyr Leu Tyr Cys Tyr Tyr
225                230                235                240
Val Ala Gly Thr Val Gly Leu Met Ser Val Pro Ile Met Gly Ile Ala
                245                250                255
Pro Asp Ser Lys Ala Thr Thr Glu Ser Val Tyr Asn Ala Ala Leu Ala
            260                265                270
Leu Gly Ile Ala Asn Gln Leu Thr Asn Ile Leu Arg Asp Val Gly Glu
        275                280                285
Asp Ala Arg Arg Gly Arg Val Tyr Leu Pro Gln Asp Glu Leu Ala Gln
290                295                300
Ala Gly Leu Ser Asp Asn Asp Ile Phe Ala Gly Lys Val Thr Asp Lys
305                310                315                320
Trp Arg Ser Phe Met Lys Lys Gln Ile Gln Arg Ala Arg Lys Phe Phe
                325                330                335
Asp Glu Ala Glu Glu Gly Val Thr Gln Leu Ser Ser Ala Ser Arg Trp
            340                345                350
Pro Val Trp Ala Ser Leu Leu Leu Tyr Arg Gln Ile Leu Asp Glu Ile
        355                360                365
```

```
Glu Ala Asn Asp Tyr Asn Asn Phe Thr Arg Arg Ala Tyr Val Ser Lys
    370             375                 380

Pro Lys Lys Leu Ile Ser Leu Pro Ile Ala Tyr Ala Lys Ser Leu Val
385             390             395                         400

Pro Pro Thr Arg Thr Leu Val Thr Ser Ser
                405                 410
```

( 2 ) INFORMATION FOR SEQ ID NO:7:

( i ) SEQUENCE CHARACTERISTICS:
       ( A ) LENGTH: 1814 base pairs
       ( B ) TYPE: nucleic acid
       ( C ) STRANDEDNESS: single
       ( D ) TOPOLOGY: linear ( i i ) MOLECULE TYPE: cDNA ( i x ) FEATURE:
       ( A ) NAME/KEY: CDS
       ( B ) LOCATION: 363..1592

( x i ) SEQUENCE DESCRIPTION: SEQ ID NO:7:

```
AGAAGAAAAA CAAAGAAACT CATTTGATTC TTGAAGAGTA CACAGCAGCA AGCAAGAAAA      60

TTAAAGTGGC TATTTTTGAA AAGCCATTGT TACAAGAAAA TTAAGAAGCC AAGAAACAGG     120

TTATTTTCTA CTTGAGTTAG GAAAAAGTTG GTTTGCTTTA TTTGTGGCTT TTTATAATCT     180

TTTTCCTCA  AGGGAAAGTG GGTATTTTCT TGAAGGTGGA TTTAGACTCT AGTGGGAATC     240

TACTAGGAGT AAATTTATTA ATTTTTTAT  AAATTAAGCA GAGGAAGGAA GGAAACAGAA     300

AACAGAAAGT AAGACAAAAA ACCTTGGAAT TGTTTAGAA  AACCAAGGTT TTCCTGTTCA     360

AA ATG TCT GTT GCC TTG TTA TGG GTT GTT TCA CCT TGT GAA GTC TCA        407
   Met Ser Val Ala Leu Leu Trp Val Val Ser Pro Cys Glu Val Ser
                   415                 420                 425

AAT GGG ACA GGA TTC TTG GAT TCA GTC CGG GAG GGA AAC CGG GTT TTT       455
Asn Gly Thr Gly Phe Leu Asp Ser Val Arg Glu Gly Asn Arg Val Phe
                430                 435                 440

GAT TCG TCG AGG CAT AGG AAT TTA GTG TGC AAT GAG AGA AAC AAG AGA       503
Asp Ser Ser Arg His Arg Asn Leu Val Cys Asn Glu Arg Asn Lys Arg
                445                 450                 455

GGT GTG AAA CAA AGG TGG AAT TTT GGT TCT GTA AGG TCT GCT ATG GTG       551
Gly Val Lys Gln Arg Trp Asn Phe Gly Ser Val Arg Ser Ala Met Val
                460                 465                 470

GCT ACA CCG GCG GGA GAA ATG GCG ACG ATG ACA TCA GAA CAG ATG GTT       599
Ala Thr Pro Ala Gly Glu Met Ala Thr Met Thr Ser Glu Gln Met Val
                475                 480                 485

TAT GAT GTG GTT TTA AAA CAA GCA GCT TTA GTG AAG AGG CAG TTG AGA       647
Tyr Asp Val Val Leu Lys Gln Ala Ala Leu Val Lys Arg Gln Leu Arg
490                 495                 500                 505

TCT GCT GAT GAT TTA GAA GTG AAG CCG GAG ATC CCT CTC CCC GGG AAT       695
Ser Ala Asp Asp Leu Glu Val Lys Pro Glu Ile Pro Leu Pro Gly Asn
                510                 515                 520

TTG AGC TTG TTG AGT GAA GCA TAT GAT AGG TGT AGT GAG GTA TGT GCA       743
Leu Ser Leu Leu Ser Glu Ala Tyr Asp Arg Cys Ser Glu Val Cys Ala
                525                 530                 535

GAG TAT GCA AAG ACA TTT TAC TTA GGA ACC ATG CTA ATG ACT CCA GAG       791
Glu Tyr Ala Lys Thr Phe Tyr Leu Gly Thr Met Leu Met Thr Pro Glu
                540                 545                 550

AGA AGA AGG GCT ATT TGG GCA ATA TAT GTG TGG TGC AGG AGA ACA GAT       839
Arg Arg Arg Ala Ile Trp Ala Ile Tyr Val Trp Cys Arg Arg Thr Asp
                555                 560                 565

GAA CTT GTT GAT GGC CCA AAC GCA TCA CAT GTT ACA CCC CAA GCC TTA       887
Glu Leu Val Asp Gly Pro Asn Ala Ser His Val Thr Pro Gln Ala Leu
```

-continued

```
          570                      575                      580                      585
GAT  AGG  TGG  GAA  GAC  CGG  CTT  GAA  GAT  GTT  TTC  AGC  GGG  CGA  CCA  TTT              935
Asp  Arg  Trp  Glu  Asp  Arg  Leu  Glu  Asp  Val  Phe  Ser  Gly  Arg  Pro  Phe
               590                           595                           600

GAT  ATG  CTC  GAT  GCT  GCT  TTG  TCC  GAT  ACT  GTT  TCC  AAG  CTT  CCA  GTT              983
Asp  Met  Leu  Asp  Ala  Ala  Leu  Ser  Asp  Thr  Val  Ser  Lys  Leu  Pro  Val
                    605                           610                           615

GAT  ATT  CAG  CCG  TTC  AGA  GAT  ATG  ATT  GAA  GGA  ATG  CGT  ATG  GAC  TTG             1031
Asp  Ile  Gln  Pro  Phe  Arg  Asp  Met  Ile  Glu  Gly  Met  Arg  Met  Asp  Leu
          620                           625                           630

AGG  AAG  TCA  AGA  TAT  AGA  AAC  TTT  GAT  GAG  CTT  TAC  CTC  TAT  TGT  TAT             1079
Arg  Lys  Ser  Arg  Tyr  Arg  Asn  Phe  Asp  Glu  Leu  Tyr  Leu  Tyr  Cys  Tyr
               635                           640                           645

TAC  GTT  GCT  GGT  ACG  GTT  GGG  TTG  ATG  AGT  GTT  CCA  ATT  ATG  GGT  ATT             1127
Tyr  Val  Ala  Gly  Thr  Val  Gly  Leu  Met  Ser  Val  Pro  Ile  Met  Gly  Ile
650                           655                           660                           665

GCA  CCT  GAT  TCA  AAG  GCA  ACA  ACA  GAG  AGC  GTA  TAT  AAT  GCA  GCT  TTG             1175
Ala  Pro  Asp  Ser  Lys  Ala  Thr  Thr  Glu  Ser  Val  Tyr  Asn  Ala  Ala  Leu
                    670                           675                           680

GCT  TTA  GGA  ATC  GCG  AAT  CAA  CTA  ACG  AAC  ATA  CTC  AGG  GAT  GTT  GGA             1223
Ala  Leu  Gly  Ile  Ala  Asn  Gln  Leu  Thr  Asn  Ile  Leu  Arg  Asp  Val  Gly
          685                           690                           695

GAA  GAT  GCC  AGA  AGA  GGA  AGA  GTC  TAC  TTA  CCT  CAA  GAT  GAA  TTA  GCA             1271
Glu  Asp  Ala  Arg  Arg  Gly  Arg  Val  Tyr  Leu  Pro  Gln  Asp  Glu  Leu  Ala
               700                           705                           710

CAG  GCA  GGT  CTC  TTC  GAC  GAT  GAC  ATA  TTT  GCT  GGA  AAA  GTG  ACT  GAT             1319
Gln  Ala  Gly  Leu  Phe  Asp  Asp  Asp  Ile  Phe  Ala  Gly  Lys  Val  Thr  Asp
          715                           720                           725

AAG  TGG  AGA  AGC  TTT  ATG  AAG  AAG  CAA  ATC  CAG  AGG  GCA  AGA  AAG  TTC             1367
Lys  Trp  Arg  Ser  Phe  Met  Lys  Lys  Gln  Ile  Gln  Arg  Ala  Arg  Lys  Phe
730                           735                           740                           745

TTC  GAT  GAG  GCA  GAG  GAG  GGA  GTT  ACA  CAA  CTG  AGC  TCA  GCT  AGC  AGA             1415
Phe  Asp  Glu  Ala  Glu  Glu  Gly  Val  Thr  Gln  Leu  Ser  Ser  Ala  Ser  Arg
                    750                           755                           760

TGG  CCT  GTA  TGG  GCA  TCT  TTG  CTG  TTG  TAC  CGC  CAA  ATA  CTG  GAC  GAG             1463
Trp  Pro  Val  Trp  Ala  Ser  Leu  Leu  Leu  Tyr  Arg  Gln  Ile  Leu  Asp  Glu
          765                           770                           775

ATT  GAA  GCC  AAT  GAC  TAC  AAC  AAC  TTC  ACA  AAG  AGA  GCT  TAT  GTG  AGC             1511
Ile  Glu  Ala  Asn  Asp  Tyr  Asn  Asn  Phe  Thr  Lys  Arg  Ala  Tyr  Val  Ser
               780                           785                           790

AAA  CCA  AAG  AAG  CTA  ATT  TCC  TTA  CCT  ATT  GCT  TAT  GCA  AAA  TCT  CTT             1559
Lys  Pro  Lys  Lys  Leu  Ile  Ser  Leu  Pro  Ile  Ala  Tyr  Ala  Lys  Ser  Leu
     795                           800                           805

GTG  CCC  CCT  ACA  AGA  ACT  CTT  GTC  ACC  TCT  AGC  TAAGGCATAG  ACATCAGATT             1612
Val  Pro  Pro  Thr  Arg  Thr  Leu  Val  Thr  Ser  Ser
810                      815                      820

TAAATTAAAG CAAGAAAGCA TATATTACTA TTAAAAAGA  AAGAATTTCT AAAGTAGATA                           1672

TTGTTGTATT GATGCCACTT GTATATCATC AAAAGTAGGT AGTAAAATCC AATATAACAA                           1732

TCTCTAGTAG TTGTATGTTC ACAATCTTAA GCCCTTTGAG GGGAATTCTT TTTGGTTCAT                           1792

TGGAAAAAAT TTTGCTGATT CG                                                                   1814
```

( 2 ) INFORMATION FOR SEQ ID NO:8:

( i ) SEQUENCE CHARACTERISTICS:
        ( A ) LENGTH: 410 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| | | | | | | | | | | | | | | |
|---|---|---|---|---|---|---|---|---|---|---|---|---|---|---|
| Met<br>1 | Ser | Val | Ala | Leu<br>5 | Leu | Trp | Val | Val | Ser<br>10 | Pro | Cys | Glu | Val | Ser<br>15 | Asn |
| Gly | Thr | Gly | Phe<br>20 | Leu | Asp | Ser | Val | Arg<br>25 | Glu | Gly | Asn | Arg | Val<br>30 | Phe | Asp |
| Ser | Ser | Arg<br>35 | His | Arg | Asn | Leu | Val<br>40 | Cys | Asn | Glu | Arg | Asn<br>45 | Lys | Arg | Gly |
| Val | Lys<br>50 | Gln | Arg | Trp | Asn | Phe<br>55 | Gly | Ser | Val | Arg | Ser<br>60 | Ala | Met | Val | Ala |
| Thr<br>65 | Pro | Ala | Gly | Glu | Met<br>70 | Ala | Thr | Met | Thr | Ser<br>75 | Glu | Gln | Met | Val | Tyr<br>80 |
| Asp | Val | Val | Leu | Lys<br>85 | Gln | Ala | Ala | Leu | Val<br>90 | Lys | Arg | Gln | Leu | Arg<br>95 | Ser |
| Ala | Asp | Asp | Leu<br>100 | Glu | Val | Lys | Pro | Glu<br>105 | Ile | Pro | Leu | Pro | Gly<br>110 | Asn | Leu |
| Ser | Leu | Leu<br>115 | Ser | Glu | Ala | Tyr | Asp<br>120 | Arg | Cys | Ser | Glu | Val<br>125 | Cys | Ala | Glu |
| Tyr | Ala<br>130 | Lys | Thr | Phe | Tyr | Leu<br>135 | Gly | Thr | Met | Leu | Met<br>140 | Thr | Pro | Glu | Arg |
| Arg<br>145 | Arg | Ala | Ile | Trp | Ala<br>150 | Ile | Tyr | Val | Trp | Cys<br>155 | Arg | Arg | Thr | Asp | Glu<br>160 |
| Leu | Val | Asp | Gly | Pro<br>165 | Asn | Ala | Ser | His | Val<br>170 | Thr | Pro | Gln | Ala | Leu<br>175 | Asp |
| Arg | Trp | Glu | Asp<br>180 | Arg | Leu | Glu | Asp | Val<br>185 | Phe | Ser | Gly | Arg | Pro<br>190 | Phe | Asp |
| Met | Leu | Asp<br>195 | Ala | Ala | Leu | Ser | Asp<br>200 | Thr | Val | Ser | Lys | Leu<br>205 | Pro | Val | Asp |
| Ile | Gln<br>210 | Pro | Phe | Arg | Asp | Met<br>215 | Ile | Glu | Gly | Met | Arg<br>220 | Met | Asp | Leu | Arg |
| Lys<br>225 | Ser | Arg | Tyr | Arg | Asn<br>230 | Phe | Asp | Glu | Leu | Tyr<br>235 | Leu | Tyr | Cys | Tyr | Tyr<br>240 |
| Val | Ala | Gly | Thr | Val<br>245 | Gly | Leu | Met | Ser | Val<br>250 | Pro | Ile | Met | Gly | Ile<br>255 | Ala |
| Pro | Asp | Ser | Lys<br>260 | Ala | Thr | Thr | Glu | Ser<br>265 | Val | Tyr | Asn | Ala | Ala<br>270 | Leu | Ala |
| Leu | Gly | Ile<br>275 | Ala | Asn | Gln | Leu | Thr<br>280 | Asn | Ile | Leu | Arg | Asp<br>285 | Val | Gly | Glu |
| Asp | Ala<br>290 | Arg | Arg | Gly | Arg | Val<br>295 | Tyr | Leu | Pro | Gln | Asp<br>300 | Glu | Leu | Ala | Gln |
| Ala<br>305 | Gly | Leu | Phe | Asp | Asp<br>310 | Ile | Phe | Ala | Gly | Lys<br>315 | Val | Thr | Asp | Lys<br>320 | |
| Trp | Arg | Ser | Phe | Met<br>325 | Lys | Lys | Gln | Ile | Gln<br>330 | Arg | Ala | Arg | Lys | Phe<br>335 | Phe |
| Asp | Glu | Ala | Glu<br>340 | Glu | Gly | Val | Thr | Gln<br>345 | Leu | Ser | Ser | Ala | Ser<br>350 | Arg | Trp |
| Pro | Val | Trp<br>355 | Ala | Ser | Leu | Leu | Leu<br>360 | Tyr | Arg | Gln | Ile | Leu<br>365 | Asp | Glu | Ile |
| Glu | Ala<br>370 | Asn | Asp | Tyr | Asn | Asn<br>375 | Phe | Thr | Lys | Arg | Ala<br>380 | Tyr | Val | Ser | Lys |
| Pro<br>385 | Lys | Lys | Leu | Ile | Ser<br>390 | Leu | Pro | Ile | Ala | Tyr<br>395 | Ala | Lys | Ser | Leu | Val<br>400 |
| Pro | Pro | Thr | Arg | Thr<br>405 | Leu | Val | Thr | Ser | Ser<br>410 | | | | | | |

( 2 ) INFORMATION FOR SEQ ID NO:9:

( i ) SEQUENCE CHARACTERISTICS:
        ( A ) LENGTH: 749 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

| | | | | | |
|---|---|---|---|---|---|
| TAAAGTTTAC | ATACTTCCCC | GAGCCCATTT | GTGGGATTTA | TGAGTTTGTT | GTTGTAAATT | 60 |
| TTTATTGATT | CAGTGGTTAT | AATTGAGTGT | TAATTGTGAT | GTTGTTTAT | CTCATTTGAG | 120 |
| AAGCAAAGAA | ACAGGTTATT | TTCTGCTTGA | GTTAGGAAAA | GCTGAGTTGC | TTTCTTTGTG | 180 |
| GTCTTTTTAT | AATCTTTTAC | ATAACAGGAA | GTAGGTATTT | TCTTGAAAGT | TGATTTAGAC | 240 |
| TCTAGTGGGA | ATCTACTAGG | AGTATTTTTT | TTATTTTTA | TTTTTATAA | ATTAAGCAGA | 300 |
| GGAGGGAAGG | AAACAGAAAA | CAGAAAGTAA | GACAAAAAAA | CCTTGGAATT | GTTTAGACA | 360 |
| ACCAAGGTTT | TGTTGTTCAG | AATGTCTGTT | GCCTTGTTAT | GGGTTGTTTC | ACCTTGTGAG | 420 |
| GTCTCAAATG | GGACAGGATT | CTTGGATTCA | GGAAGGGAGG | GAAACCGGGT | TTTTGACTCG | 480 |
| TCGAGGCATA | GGAATTTAGT | GTGCAATGAG | AGAATCAAAA | GAGGTGTGAA | ACAAAGGTGG | 540 |
| AATTTGGTT | CCGTACGGTC | TGCGATGGTG | GCTACACCAA | CGGGAGAAAT | GGCGACAATG | 600 |
| ACATCAGAAC | AGAAGGTTTA | TGATGTGGTA | TTGAAACAAG | CAGCTTTAGT | GAAAAGGCAG | 660 |
| CTGAGATCTA | CTGATGATTT | AGAAGTGAAG | CCGGAGATCC | CTCTCCCCGG | GAATTTGAGC | 720 |
| TTGTTAAGTG | AAGCATATGA | TAGGTGTAG | | | | 749 |

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

TATGTATGGT GCAGAAGAAC AGAT                                    24

( 2 ) INFORMATION FOR SEQ ID NO:11:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

AGTCGACTCT TCCTCTTCTG GCATC                                 25

( 2 ) INFORMATION FOR SEQ ID NO:12:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

GGCCACGCGT CGACTAGTAC TTTTTTTTTT TTTTTTT 37

( 2 ) INFORMATION FOR SEQ ID NO:13:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:13:

AGCGGGCGAC CATTTGATAT GCTCG 25

( 2 ) INFORMATION FOR SEQ ID NO:14:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:14:

CATCAACCCA ACCGTACCAG CAACG 25

( 2 ) INFORMATION FOR SEQ ID NO:15:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:15:

ACTTCCTCAA GTCCATACGC ATTCC 25

( 2 ) INFORMATION FOR SEQ ID NO:16:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:16:

CTACACCTAT CATATGCTTC AC 22

( 2 ) INFORMATION FOR SEQ ID NO:17:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:17:

GCTCCATATG TCTGTTGCCT TGTTATGG 28

(2) INFORMATION FOR SEQ ID NO:18:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

TCGGATCCCT ATGCCTTAGC TATAGAGG        28

(2) INFORMATION FOR SEQ ID NO:19:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

TCGGATCCTT AGCTAGAGGT GACAAGAG        28